(12) United States Patent
Biris et al.

(10) Patent No.: US 10,195,228 B2
(45) Date of Patent: Feb. 5, 2019

(54) MULTICOMPONENT AND BIOCOMPATIBLE NANOCOMPOSITE MATERIALS, METHODS OF SYNTHESIZING SAME AND APPLICATIONS OF SAME

(71) Applicant: BOARD OF TRUSTEES OF THE UNIVERSITY OF ARKANSAS, Little Rock, AR (US)

(72) Inventors: Alexandru S. Biris, Little Rock, AR (US); Alexandru R. Biris, Cluj Napoca (RO)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 88 days.

(21) Appl. No.: 14/815,259

(22) Filed: Jul. 31, 2015

(65) Prior Publication Data
US 2015/0335789 A1    Nov. 26, 2015

Related U.S. Application Data

(62) Division of application No. 14/258,288, filed on Apr. 22, 2014, now Pat. No. 9,114,134, which is a division of application No. 13/599,394, filed on Aug. 30, 2012, now Pat. No. 8,741,318.

(60) Provisional application No. 61/532,810, filed on Sep. 9, 2011.

(51) Int. Cl.
| | |
|---|---|
| A61L 27/42 | (2006.01) |
| A61K 33/42 | (2006.01) |
| A61L 27/54 | (2006.01) |
| A61L 27/12 | (2006.01) |
| A61L 27/04 | (2006.01) |
| A61K 9/00 | (2006.01) |

(52) U.S. Cl.
CPC ............ *A61K 33/42* (2013.01); *A61K 9/0087* (2013.01); *A61L 27/047* (2013.01); *A61L 27/12* (2013.01); *A61L 27/422* (2013.01); *A61L 27/54* (2013.01); *A61L 2400/12* (2013.01); *A61L 2430/02* (2013.01)

(58) Field of Classification Search
None
See application file for complete search history.

(56) References Cited

U.S. PATENT DOCUMENTS

2010/0104652 A1 * 4/2010 Biris ............... A61K 9/5115
424/490

OTHER PUBLICATIONS

"Cytotoxicity Effects of Graphene and Single-Wall Carbon Nanotuibes in Neural Phaeochromocytoma-Derived PC12 Cells," Zhang, Y., et al., ACS Nano 4(6): 3181-3186 (published online May 28, 2010).*

Biris, A.R., et al., Journal of Physical Chemistry 115: 18967-18976 (published Aug. 24, 2011).*
Gupta, Y., et al., Bioorganic & Medicinal Chemistry Letters 16: 363-366 (2006).*
Yoshikawa, H. et al., Bone tissue engineering with porous hydroxyapatite ceramis, J. Artif. Organs, 2005, 8, 131-136.
Yeong, W-Y. et al., Rapid prototyping in tissue engineering: challenges and potential, Trends in Biotechnology, 2004, 22, 12, 643-652.
Fang, L. et al., Processing and mechanical properties of HA/UHMWPE nanocomposites, Biomaterials, 2006, 27, 3701-3707.
Chang, M.C. et al., Preparation of hydroxyapatite-gelatin nanocomposite, Biomaterials, 2003, 24, 2853-2862.
Chen, B. et al., Mechanical and dynamic viscoelastic properties of hydroxyapatite reinforced poly (ε-caprolactone), Polymer Testing, 2005, 24, 978-982.
Li, J. et al., Hydroxyapatite-alumina composites and bone-bonding, Biomaterials, 1995, 16, 417-422.
Malik, M.A. et al., Osteoblasts on hydroxyapatite, alumina and bone surfaces in vitro: morphology during the first 2 h of attachment, Biomaterials, 1992, 13, 2, 123-128.
Zheng, X. et al., Bond strength of plasma-sprayed hydroxyapatite/Ti composite coatings, Biomaterials, 2000, 21, 841-849.
Kim, H-M et al., Preparation of bioactive Ti and its alloys via simple chemical surface treatment, J. of Biomed. Mat. Res., 1996, 32, 409-417.
Dervishi, E. et al., Thermally controlled synthesis of single-wall carbon nanotubes with selective diameters, J. Mat. Chem., 2009, 19, 3004-3012.
Biris, A. R. et al., High-Quality Double-Walled carbon nanotubes grown by a cold-walled radio frequency chemical vapor deposition process, Chem. Mater., 2008, 20, 3466-3472.
Li, Z. et al., Does the wall number of carbon nanotubes matter as conductive transparent material? App. Phys. Lett., 2007, 91, 5.
Krishnan, A. et al., Young's modulus of single-walled nanotubes, J. Phys. Rev. B 58, 1998, 58, 20, 14013-14019.
Shokuhfar, T. et al., Prediction of the Mechanical Properties of Hydroxyapatite/Polymethyl Methacrylate/Carbon Nanotubes Nanocomposite, J. Nanosc. and Nanotechnol., 2008, 8, 4279-4284.
Zhao, B. et al., A bone mimic based on the self-assembly of hydroxyapatite on chemically functionalized single-walled carbon nanotubes, Chem. Mater., 2005, 17, 3235-3241.
Liao, S. et al., Self-assembly of nano-hydroxyapatite on multi-walled carbon nanotubes, Acta Biomater., 2007, 3, 669-675.
Omori, M. et al., Nanocomposite prepared from carbon nanotubes and hydroxyapatite precursors, Nano Biomedicine, 2009, 1, 2, 137-142.

(Continued)

*Primary Examiner* — David J Blanchard
*Assistant Examiner* — Daniel F. Coughlin
(74) *Attorney, Agent, or Firm* — Locke Lord LLP; Tim Tingkang Xia, Esq.

(57) ABSTRACT

One aspect of the present invention relates to a multicomponent and biocompatible nanocomposite material, including a graphene structure formed with a plurality of graphene layers; and gold/hydroxyapatite (Au/HA) nanoparticles distributed within the graphene structure; where the nanocomposite material is formed by heating an Au/HA catalyst thin film with a carbon source gas to perform radio frequency chemical vapor deposition (RF-CVD).

11 Claims, 10 Drawing Sheets

(56) References Cited

OTHER PUBLICATIONS

White, A. A. et al., Optimization of the sintering atmosphere for high-density hydroxyapatite-carbon nanotube composites, J. R. Soc. Interface, 2010, 7, 529-539.
Lu, X. et al., In situ growth of carbon nanotubes in hydroxyapatite matrix by chemical vapor deposition, Advanced Materials Research, 2009, 79-82, 1671-1674.
Li, H. et al., Dispersion of carbon nanotubes in hydroxyapatite powder by in situ chemical vapor deposition, Materials Science and Engineering B, 2010, 166, 19-23.
Novoselov, K.S. et al., Electric Field Effect in Atomically Thin Carbon Films, Science, 2004, 306, 666.
Fan, H. et al., Fabrication, mechanical properties, and biocompatibility of graphene-reinforced chitosan composites, Biomacromolecules, 2010, 11, 2345-2351.
Zhang, Y. et al., Cytotoxicity effects of graphene and single-wall carbon nanotubes in neural phaeochromocytoma-derived PC12 cells, ACS Nano., 2010, 4, 6, 3181-3186.
Lupu, D. et al., Carbon nanostructures produced by CCVD with induction heating, Carbon, 2004, 42, 503-507.
Biris, A. R. et al., Catalyst excitation by radio frequency for improved carbon nanotubes synthesis, Chem. Phys. Lett., 2006, 429, 204-208.
Sing, K.S.W. et al., Reporting physisorption Data for gas-solid systems with special reference to the determination of surface area and porosity, Pure & Appl. Chem., 1985, 57, 4, 603-619.
Bouropoulos, N. et al., Dynamic mechanical properties of calcium alginate-hydroxyapatite nanocomposite hydrogels, Science of Advanced Materials, 2010, 2, 239-242.
Dervishi, E. et al., The role of hydrocarbon concentration on the synthesis of large area few to multi-layer graphene structures, Chem. Phys. Lett., 2011, 501, 390-295.
Moon, J.-M. et al., High-Yield purification process of singlewalled carbon nanotubes, Phys.Chem. B, 2001, 105, 5677-5681.
Dillon, A. C. et al., A simple and Complete purification of single-walled carbon nanotube materials, Adv. Mater., 1999, 11, 16, 1354.
Gregg, S. B. et al., Thermogravimetric analysis of synthesis variation effects on CVD generated multiwalled carbon nanotubes, J. Phys. Chem. B, 2006, 110, 1179-1186.
Ramesh, P. et al., Purification and characterization of double-wall carbon nanotubes synthesized by catalytic chemical vapor deposition on mesoporous silica, Chem. Phys. Lett., 2006, 418, 408-412.
Dresselhaus, M. S. et al., Perspectives on carbon nanotubes and graphene raman spectroscopy, Nano Letters, 2010, 10,751-758.
Hojati-Talemi, P. et al., Preparation of graphene nanowalls by a simple microwave-based method, Carbon, 2010, 48, 3993-4000.
Park, J. S. et al., G' band raman spectra of single, double and triple layer graphene, Carbon, 2009, 47, 1303-1310.
Ferrari, A. C. Raman spectroscopy of graphene and graphite: disorder, electron-phonon coupling, doping and nonadiabatic effects, Solid State Communications, 2007, 143, 47-57.
De Aza, P. N. et al., Vibrational properties of calcium phosphate compounds. 2. Comparison between hydroxyapatite and β-Tricalcium phosphate, Chem. Mater., 1997, 9, 916-922.
Zanello, L. P. et al., Bone cell proliferation on carbon nanotubes, Nano Letters, 2006, 6, 3, 562-567.
Mahmood, M. et al., Enhanced bone cells growth and proliferation on TiO2 nanotubular substrates treated by RF plasma discharge, Adv. Engin. Mat., 2011, 13, 3, B95-B101.

\* cited by examiner

MULTICOMPONENT AND BIOCOMPATIBLE NANOCOMPOSITE MATERIALS, METHODS OF SYNTHESIZING SAME AND APPLICATIONS OF SAME

CROSS-REFERENCE TO RELATED PATENT APPLICATIONS

This application is a divisional application of, and claims the benefit of U.S. patent application Ser. No. 14/258,288, filed Apr. 22, 2014, entitled "MULTICOMPONENT AND BIOCOMPATIBLE NANOCOMPOSITE MATERIALS, METHODS OF SYNTHESIZING SAME AND APPLICATIONS OF SAME", by Alexandru S. Biris and Alexandru R. Biris, now allowed, which itself is a divisional application of, and claims the benefit of U.S. patent application Ser. No. 13/599,394, filed Aug. 30, 2012, entitled "MULTICOMPONENT AND BIOCOMPATIBLE NANOCOMPOSITE MATERIALS, METHODS OF SYNTHESIZING SAME AND APPLICATIONS OF SAME", by Alexandru S. Biris and Alexandru R. Biris, now U.S. Pat. No. 8,741,318, which itself claims priority to and the benefit of, pursuant to 35 U.S.C. § 119(e), U.S. Provisional Patent Application Ser. No. 61/532,810, filed Sep. 9, 2011, entitled "MULTICOMPONENT AND BIOCOMPATIBLE NANOCOMPOSITE MATERIALS AND APPLICATIONS OF SAME," by Alexandru S. Biris and Alexandru R. Biris. Each of the above disclosures is incorporated herein in its entirety by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [10] represents the 10th reference cited in the reference list, namely, Dervishi, E.; Li, Z.; Watanabe, F., Xu, Y.; Saini, V.; Biris, A. R.; Biris, A. S. *J. Mat. Chem.*, 2009, 19, 3004-3012.

FIELD OF THE INVENTION

The present invention relates generally to nanocomposite materials, and more particularly to multicomponent and biocompatible nanocomposite materials, methods of synthesizing the same, and applications of the same.

BACKGROUND OF THE INVENTION

Calcium phosphate, $Ca_{10}(PO_4)_2(OH)_2$, also known as hydroxyapatite (HA), is the major component of natural bone tissues and is characterized by an excellent biocompatibility; as a result, it is currently widely used in various forms and shapes in bone and tissue engineering [1]. Nonetheless, the mechanical properties of hydroxyapatite, such as its low toughness of about 0.8-1.2 MP and low flexural strength (less than about 140 MPa), limit its use in the regeneration of various parts of the bone systems, especially those under significant mechanical tension. Moreover, the difficulty of generating three-dimensional (3D) bone re-growth structures from HA further restricts its use in the regeneration of complex bone systems [2].

In order to overcome these limitations, a number of HA-based composite materials has been developed and studied based on both natural and synthetic polymers [3-5] with inorganic compounds such as alumina ($Al_2O_3$) [6, 7], titanium (Ti) or Ti alloys [8, 9]. The characteristics of the carbon nanotubes (CNTs), such as high aspect ratio (hundreds or thousands) [10, 11], a good electrical[12] and thermal conductivity, and excellent mechanical properties (modulus of elasticity of about 1.25 TPa) [13], suggest that these materials could be an excellent candidate for a scaffold or as a doping agent in the composites used for bone engineering. It has been shown [14] that the utilization of CNTs along with HA and polymethyl methacrylate (PMMA) resulted in the development of a new composite material with superior mechanical properties as compared to those without the CNT addition for biomedical scaffolding in bone engineering and regeneration. Previous studies have reported the use of both single-walled carbon nanotubes (SWCNTs) [15] and multi-walled carbon nanotubes (MW-CNTs) for such applications [16, 17].

However, it remains extremely difficult to accomplish a perfectly homogeneous composition of the CNT-based composites by traditional mixing technology, given the possible development of defects in the nanotube walls, with major influences on the macroscopic properties of the composites. To overcome this limitation, the development of such composites is performed through sintering [18] or in-situ growth of the CNTs in the HA matrix [19] or over the catalytic Fe, Ni, and Co nanoparticles supported on the surface of HA [20].

Therefore, a heretofore unaddressed need exists in the art to address the aforementioned deficiencies and inadequacies.

SUMMARY OF THE INVENTION

One aspect of the present invention relates to a method of synthesizing a multicomponent and biocompatible nanocomposite material, which includes: immersing hydroxyapatite (HA) nanocrystals and gold trichloride trihydrate ($HAuCl_4.3H_2O$) in water to form a mixture; stirring the mixture at about 80° C. such that gold (Au) nanoparticles deposits on the HA nanocrystals; drying the mixture at about 100° C. to form an Au/HA catalyst; distributing the Au/HA catalyst in a crucible to form a thin film; and heating the thin film in a reactor with a carbon source gas to perform radio frequency chemical vapor deposition (RF-CVD) to form the nanocomposite material, where the nanocomposite material includes a graphene structure and Au/HA nanoparticles formed by the Au/HA catalyst and distributed within the graphene structure.

In one embodiment, the heating of the thin film with the carbon source gas includes: introducing an inert gas to the reactor at a first flow rate for a first time; heating the crucible in the reactor to a first temperature; introducing hydrogen to the reactor at a second flow rate for a second time; heating the reactor to a second temperature; introducing the carbon source gas to the reactor at a third flow rate for a third time; and cooling the reactor. In a further embodiment, the inert gas includes Ar. In some embodiments, the first flow rate is about 150-600 ml/min, and the first period is about 5-20 minutes; the second flow rate is about 50-300 ml/min, and the second period is about 5-20 minutes; and the first temperature is about 400-600° C.

In one embodiment, the carbon source gas includes acetylene ($C_2H_2$). In a further embodiment, the second temperature is about 750-900° C., the third flow rate is about 5-30 ml/min, and the third time is about 15-90 minutes.

In one embodiment, the carbon source gas includes methane ($CH_4$). In a further embodiment, the second temperature is about 850-1000° C., the third flow rate is about 40-240 ml/min, and the third time is about 15-60 minutes.

In another aspect, the present invention relates to a multicomponent and biocompatible nanocomposite material. In one embodiment, the nanocomposite material includes a graphene structure formed with a plurality of graphene layers; and Au/HA nanoparticles distributed within the graphene structure. The nanocomposite material is formed by heating an Au/HA catalyst thin film with a carbon source gas to perform RF-CVD. In some embodiments, the graphene structure includes few-layer graphene.

In one embodiment, the carbon source gas includes acetylene. In one embodiment, the carbon source gas includes methane.

In one embodiment, the Au/HA catalyst thin film is formed by: immersing HA nanocrystals and gold trichloride trihydrate in a liquid to form a mixture; stirring the mixture at a stirring temperature such that Au nanoparticles deposits on the HA nanocrystals; drying the mixture at a drying temperature to obtain the Au/HA catalyst; and distributing the Au/HA catalyst to form the Au/HA catalyst thin film. In a further embodiment, the stirring temperature is about 70-90° C., and the drying temperature is about 100° C.

A further aspect of the present invention relates to a method of synthesizing a multicomponent and biocompatible nanocomposite material, which includes: synthesizing an Au/HA catalyst; distributing the Au/HA catalyst into a thin film; and heating the thin film in a reactor with a carbon source gas to perform RF-CVD to form the nanocomposite material, where the nanocomposite material includes a graphene structure and Au/HA nanoparticles formed by the Au/HA catalyst and distributed within the graphene structure.

In one embodiment, the Au/HA catalyst is synthesized by: immersing HA nanocrystals and gold trichloride trihydrate in a liquid to form a mixture; stirring the mixture at a stirring temperature such that Au nanoparticles deposits on the HA nanocrystals; and drying the mixture at a drying temperature to obtain the Au/HA catalyst. In a further embodiment, the stirring temperature is about 70-90° C., and the drying temperature is about 100° C.

In one embodiment, heating of the thin film with the carbon source gas includes: introducing an inert gas to the reactor at a first flow rate for a first time; heating the reactor to a first temperature; introducing hydrogen to the reactor at a second flow rate for a second time; heating the reactor to a second temperature; and introducing the carbon source gas to the reactor at a third flow rate for a third time. In a further embodiment, the inert gas includes Ar. In some embodiments, the first flow rate is about 150-600 ml/min, and the first period is about 5-20 minutes; the second flow rate is about 50-300 ml/min, and the second period is about 5-20 minutes; and the first temperature is about 400-600° C.

In one embodiment, the carbon source gas includes acetylene. In a further embodiment, the second temperature is about 750-900° C., the third flow rate is about 5-30 ml/min, and the third time is about 15-90 minutes.

In one embodiment, the carbon source gas includes methane. In a further embodiment, the second temperature is about 850-1000° C., the third flow rate is about 40-240 ml/min, and the third time is about 15-60 minutes.

In another aspect, the present invention relates to a method of regenerating bone tissues. In one embodiment, the method includes: synthesizing a multicomponent and biocompatible nanocomposite material, including: (i) synthesizing an Au/HA catalyst; (ii) distributing the Au/HA catalyst into a thin film; and (iii) heating the thin film in a reactor with a carbon source gas to perform RF-CVD to form the nanocomposite material, where the nanocomposite material includes a graphene structure and Au/HA nanoparticles formed by the Au/HA catalyst and distributed within the graphene structure; and applying the nanocomposite material in an area of bone regeneration.

In yet another aspect, a method of regenerating bone tissues includes: synthesizing a multicomponent and biocompatible nanocomposite material, the nanocomposite material including a graphene structure formed with a plurality of graphene layers and Au/HA nanoparticles distributed within the graphene structure; and applying the nanocomposite material in an area of bone regeneration. The nanocomposite material is formed by heating an Au/HA catalyst thin film with a carbon source gas to perform RF-CVD.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment.

DETAILED DESCRIPTION OF THE INVENTION

Figure 1A:
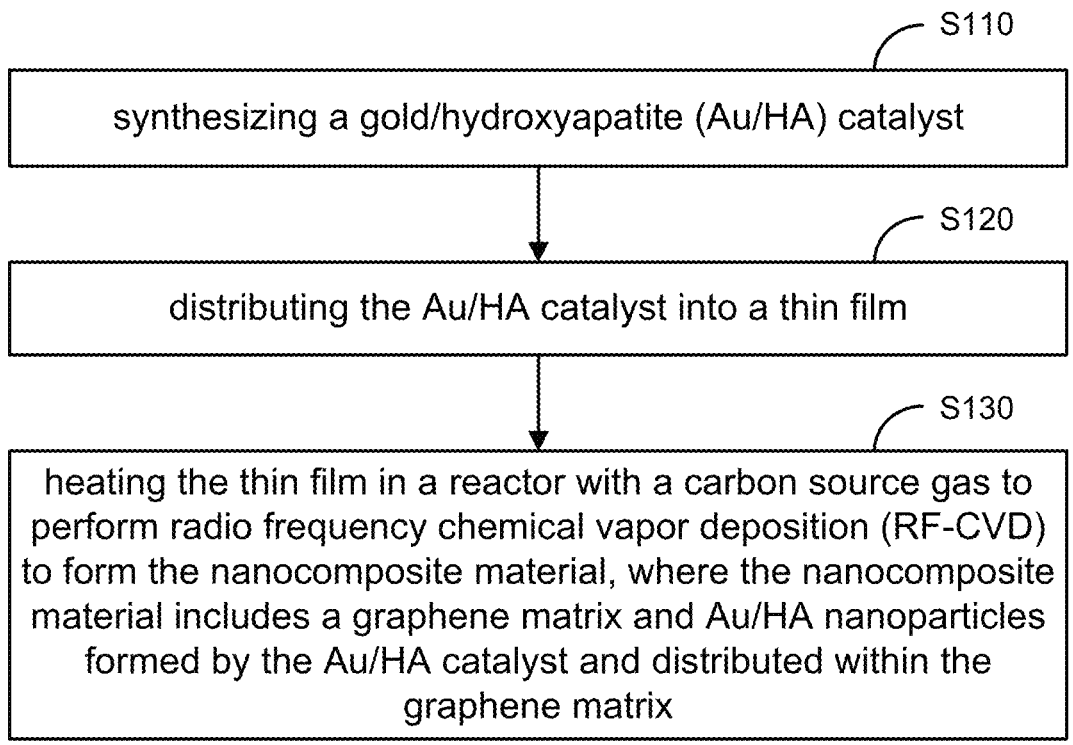
FIG. 1A shows a flowchart of synthesizing a multicomponent and biocompatible nanocomposite material according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "plurality" means two or more.

As used herein, the terms "comprising", "including", "carrying", "having", "containing", "involving", and the like are to be understood to be open-ended, i.e., to mean including but not limited to.

The terms "scanning electron microscope" or its abbreviation "SEM", as used herein, refers to a type of electron microscope that images the sample surface by scanning it with a high-energy beam of electrons in a raster scan pattern. The electrons interact with the atoms that make up the sample producing signals that contain information about the sample's surface topography, composition and other properties such as electrical conductivity.

The term "transmission electron microscope" or its abbreviation "TEM", as used herein, refers to a microscope formed with the microscopy technique whereby a beam of electrons is transmitted through an ultra thin specimen, interacting with the specimen as it passes through. An image is formed from the interaction of the electrons transmitted through the specimen; the image is magnified and focused onto an imaging device, such as a fluorescent screen, on a layer of photographic film, or to be detected by a sensor such as a CCD camera.

As used herein, if any, the term "scanning transmission electron microscope" or its abbreviation "STEM" refers to a type of TEM. STEM is distinguished from conventional TEM by focusing the electron beam into a narrow spot which is scanned over the sample in a raster.

As used herein, if any, the term "annular dark-field imaging" is a method of mapping samples in a STEM. These images are formed by collecting scattered electrons with an annular dark-field detector. The term "high-angle annular dark-field imaging" or its abbreviation "HAAD" or "HAADF", as used herein, refers to the technique of forming an annular dark field image only by very high angle, incoherently scattered electrons—as opposed to Bragg scattered electrons—which is highly sensitive to variations in the atomic number of atoms in the sample (Z-contrast images).

As used herein, if any, the term "energy-dispersive X-ray spectroscope" or its abbreviation "EDS" refers to an analytical technique used for the elemental analysis or chemical characterization of a sample. It relies on the investigation of an interaction of some source of X-ray excitation and a sample. Its characterization capabilities are due in large part to the fundamental principle that each element has a unique atomic structure allowing unique set of peaks on its X-ray spectrum.

As used herein, the term "thermogravimetric analysis" or its abbreviation "TGA" refers to a type of testing performed on samples that determines changes in weight in relation to a temperature program in a controlled atmosphere. Such analysis relies on a high degree of precision in three measurements: weight, temperature, and temperature change. Specifically, TGA is the process of heating a mixture to a high enough temperature so that one of the components decomposes into a gas, which dissociates into the air. The TGA process utilizes heat and stoichiometry ratios to determine the percent by mass ratio of a solute.

As used herein, if any, the term "differential thermal analysis" or its abbreviation "DTA" is a thermoanalytic technique, similar to differential scanning calorimetry. In DTA, the material under study and an inert reference are made to undergo identical thermal cycles, while recording any temperature difference between sample and reference. This differential temperature is then plotted against time, or against temperature (DTA curve or thermogram). Thus, a DTA curve provides data on the transformations that have occurred to.

The term "Raman spectrum", as used herein, refers to a spectrum obtained using the spectroscopic technique of Raman spectroscopy to study vibrational, rotational, and other low-frequency modes in a system. Raman spectroscopy relies on inelastic scattering, or Raman scattering, of monochromatic light, usually from a laser in the visible, near infrared, or near ultraviolet range. The laser light interacts with molecular vibrations, phonons or other excitations in the system, resulting in the energy of the laser photons being shifted up or down. The shift in energy gives information about the vibrational modes in the system.

As used herein, the term "3-(4,5-Dimethylthiazol-2-yl)-2,5-diphenyltetrazolium bromide" or its abbreviation "MTT" refers to a yellow tetrazole, which is reduced to purple formazan in living cells. A solubilization solution can be added to dissolve the insoluble purple formazan product into a colored solution. The absorbance of this colored solution can be quantified by measuring at a certain wavelength (usually between about 500 and about 600 nm) by a spectrophotometer. MTT may be applied to assess the viability (cell counting) and the proliferation of cells (cell culture assays) or to determine cytotoxicity of potential medicinal agents and toxic materials, since those agents would stimulate or inhibit cell viability and growth.

As used herein, the term "lactate dehydrogenase" or its abbreviation "LDH" refers to an enzyme (biological molecules that catalyze chemical reactions) present in a wide variety of organisms, including plants and animals. Tissue breakdown releases LDH, and therefore LDH can be measured as a surrogate for tissue breakdown, e.g., hemolysis. Other disorders indicated by elevated LDH include cancer, meningitis, encephalitis, acute pancreatitis, and HIV.

As used herein, "nanoscopic-scale", "nanoscopic", "nanometer-scale", "nanoscale", "nanocomposites", "nanoparticles", the "nano-" prefix, and the like generally refers to elements or articles having widths or diameters of less than about 1 µm, preferably less than about 100 nm in some cases. In all embodiments, specified widths can be smallest width (i.e. a width as specified where, at that location, the article can have a larger width in a different dimension), or largest width (i.e. where, at that location, the article's width is no wider than as specified, but can have a length that is greater).

As used herein, a "nanostructure" refers to an object of intermediate size between molecular and microscopic (micrometer-sized) structures. In describing nanostructures, the sizes of the nanostructures refer to the number of dimensions on the nanoscale. For example, nanotextured surfaces have one dimension on the nanoscale, i.e., only the thickness of the surface of an object is between about 0.1 and about 1000 nm. A list of nanostructures includes, but not limited to, nanoparticle, nanocomposite, quantum dot, nanofilm, nanoshell, nanofiber, nanoring, nanorod, nanowire, nanotube, nanocapillary structures, and so on.

Overview of the Invention

The present invention relates to nanocomposite materials, methods of synthesizing the same, and applications of the same. The nanocomposite material includes a graphene structure formed with a plurality of graphene layers; and gold/hydroxyapatite (Au/HA) nanoparticles distributed within the graphene structure. The nanocomposite material is formed by synthesizing an Au/HA catalyst, distributing the Au/HA catalyst into a thin film, and heating the thin film with a carbon source gas to perform radio frequency chemical vapor deposition (RF-CVD) such that the graphene structure is formed with the Au/HA nanoparticles distributed therein.

Recently discovered carbon-based two-dimensional (2D) nanostructures, known as graphenes [21], have electrical, thermal, and mechanical properties relatively similar to those of the carbon nanotubes (but in a 2D manner) and, as a result, have potential for use in major scientific and technological applications. In the bio-medical processes, graphenes have been used along with chitosan in composites that were reported to show a 200 times increase in the elasticity modulus compared to undoped chitosan [22]. The cytotoxic effects of these 2D materials have recently been studied in comparison to those of the SWCNTs, and it has been shown that the graphene layers induce fewer undesirable toxic effects [23]. The development of novel multifunctional nanosystems for bone regeneration should therefore use nanomaterials with low toxicity in order for the final composite not to be rejected or induce tissue inflammation once introduced inside the organism.

Taking into consideration that gold nanoparticles (Au NPs) do not exhibit significant cytotoxicity in biological systems and based on the goal to develop low toxicity multi-component nanocomposite materials, the present invention discloses the in situ synthesis of few-layer graphenes over an Au/HA nanocomposite catalyst by using the method of radio-frequency chemical vapor deposition (RF-CVD) [11, 24, 25]. The catalytic activity of Au nanoclusters supported over HA nanoparticles has not been previously studied with respect to the growth of highly ordered graphitic structures and in particular to the generation of few-layer graphenes. According to the present invention such nanocomposite materials (also referred hereinafter to as "Au/HA@graphene") can be synthesized in situ by one stem growth process and that they present high bio-compatibility towards the proliferation of bone-osteoblast cells in vitro.

One aspect of the present invention discloses a synthesis method of few-layer graphenes over a novel Au/hydroxyapatite catalytic system by RF-CVD, with acetylene and methane as the carbon sources. The synthesis time is found to influence linearly the dimensions of the graphitic layers and asymptotically their corresponding thermal decomposition temperature. The resulting multicomponent nanocomposite material formed out of graphene layers, Au nanoparticles supported on the surface of hydroxyapatite nanoparticles, is found to have good biocompatibility and induce excellent bone cellular proliferation. Such multicomponent composites can find excellent applications in the area of bone regeneration given the excellent biocompatibility, 3D structure, and unique composition. The multicomponent composites can be further included in other more complex tissue (bone) regeneration scaffolds. Some of these scaffolds could be based on polymeric nanomaterials that are decorated with antibiotics and growth factors. Also, Au/HA@Graphene could be decorated by themselves with genes, antibiotics, or growth factors.

In one embodiment, the method of synthesizing a multicomponent and biocompatible nanocomposite material includes: immersing HA nanocrystals and $HAuCl_4.3H_2O$ in water to form a mixture; stirring the mixture at about 80° C. such that Au nanoparticles deposits on the HA nanocrystals; drying the mixture at about 100° C. to form an Au/HA catalyst; distributing the Au/HA catalyst in a crucible to form a thin film; and heating the thin film in a reactor with a carbon source gas to perform RF-CVD to form the nanocomposite material, where the nanocomposite material includes a graphene structure and Au/HA nanoparticles formed by the Au/HA catalyst and distributed within the graphene structure.

In one embodiment, the heating of the thin film with the carbon source gas includes: introducing an inert gas to the reactor at a first flow rate for a first time; heating the crucible in the reactor to a first temperature; introducing hydrogen to the reactor at a second flow rate for a second time; heating the reactor to a second temperature; introducing the carbon source gas to the reactor at a third flow rate for a third time; and cooling the reactor. In a further embodiment, the inert gas includes Ar. In some embodiments, the first flow rate is about 150-600 ml/min, and the first period is about 5-20 minutes; the second flow rate is about 50-300 ml/min, and the second period is about 5-20 minutes; and the first temperature is about 400-600° C.

In one embodiment, the carbon source gas includes acetylene ($C_2H_2$). In a further embodiment, the second temperature is about 750-900° C., the third flow rate is about 5-30 ml/min, and the third time is about 15-90 minutes.

In one embodiment, the carbon source gas includes methane ($CH_4$). In a further embodiment, the second temperature is about 850-1000° C., the third flow rate is about 40-240 ml/min, and the third time is about 15-60 minutes.

In another aspect, the present invention relates to a multicomponent and biocompatible nanocomposite material. In one embodiment, the nanocomposite material includes a graphene structure formed with a plurality of graphene layers; and Au/HA nanoparticles distributed within the graphene structure. The nanocomposite material is formed by heating an Au/HA catalyst thin film with a carbon source gas to perform RF-CVD.

In one embodiment, the carbon source gas includes acetylene. In one embodiment, the carbon source gas includes methane.

In one embodiment, the Au/HA catalyst thin film is formed by: immersing HA nanocrystals and gold trichloride trihydrate in a liquid to form a mixture; stirring the mixture at a stirring temperature such that Au nanoparticles deposits on the HA nanocrystals; drying the mixture at a drying temperature to obtain the Au/HA catalyst; and distributing the Au/HA catalyst to form the Au/HA catalyst thin film. In a further embodiment, the stirring temperature is about 70-90° C., and the drying temperature is about 100° C.

A further aspect of the present invention relates to a method of synthesizing a multicomponent and biocompatible nanocomposite material, which includes: synthesizing an Au/HA catalyst; distributing the Au/HA catalyst into a thin film; and heating the thin film in a reactor with a carbon source gas to perform RF-CVD to form the nanocomposite material, where the nanocomposite material includes a graphene structure and Au/HA nanoparticles formed by the Au/HA catalyst and distributed within the graphene structure.

In one embodiment, the Au/HA catalyst is synthesized by: immersing HA nanocrystals and gold trichloride trihydrate in a liquid to form a mixture; stirring the mixture at a stirring temperature such that Au nanoparticles deposits on the HA nanocrystals; and drying the mixture at a drying temperature to obtain the Au/HA catalyst. In a further embodiment, the stirring temperature is about 70-90° C., and the drying temperature is about 100° C.

In one embodiment, heating of the thin film with the carbon source gas includes: introducing an inert gas to the reactor at a first flow rate for a first time; heating the reactor to a first temperature; introducing hydrogen to the reactor at a second flow rate for a second time; heating the reactor to a second temperature; and introducing the carbon source gas to the reactor at a third flow rate for a third time. In a further embodiment, the inert gas includes Ar. In some embodiments, the first flow rate is about 150-600 ml/min, and the first period is about 5-20 minutes; the second flow rate is about 50-300 ml/min, and the second period is about 5-20 minutes; and the first temperature is about 400-600° C.

In one embodiment, the carbon source gas includes acetylene. In a further embodiment, the second temperature is about 750-900° C., the third flow rate is about 5-30 ml/min, and the third time is about 15-90 minutes.

In one embodiment, the carbon source gas includes methane. In a further embodiment, the second temperature is about 850-1000° C., the third flow rate is about 40-240 ml/min, and the third time is about 15-60 minutes.

In another aspect, the present invention relates to a method of regenerating bone tissues. In one embodiment, the method includes: synthesizing a multicomponent and biocompatible nanocomposite material by the synthesizing method as discussed above; and applying the nanocomposite material in an area of bone regeneration.

In yet another aspect, a method of regenerating bone tissues includes: synthesizing a multicomponent and biocompatible nanocomposite material having the structure as discussed above; and applying the nanocomposite material in an area of bone regeneration. The nanocomposite material is formed by heating an Au/HA catalyst thin film with a carbon source gas to perform RF-CVD.

These and other aspects of the present invention are more specifically described below.

Implementations and Examples of the Invention

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

FIG. 1A shows a flowchart of synthesizing a multicomponent and biocompatible nanocomposite material according to one embodiment of the present invention. As shown in FIG. 1A, according to one aspect of the present invention, a method of synthesizing a multicomponent and biocompatible nanocomposite material includes: synthesizing an Au/HA catalyst (step S110); distributing the Au/HA catalyst into a thin film (step S120); and heating the thin film in a reactor with a carbon source gas to perform radio frequency chemical vapor deposition (RF-CVD) to form the nanocomposite material, where the nanocomposite material includes a graphene structure and Au/HA nanoparticles formed by the Au/HA catalyst and distributed within the graphene structure (step S130).

Figure 1B:
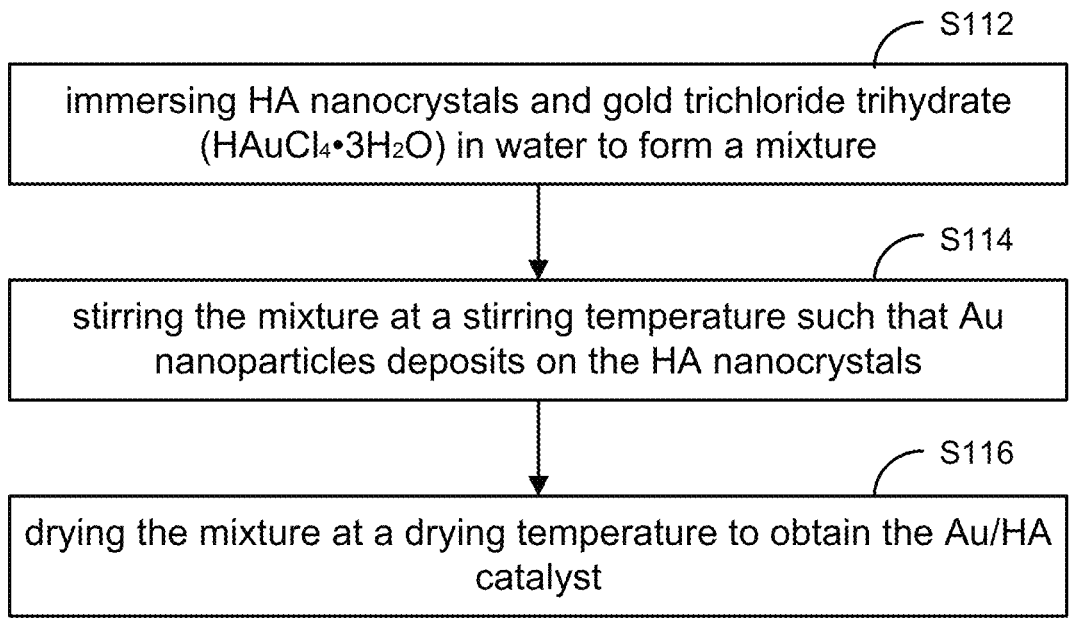
FIG. 1B shows a flowchart of synthesizing the Au/HA catalyst according to one embodiment of the present invention.

FIG. 1B shows a flowchart of synthesizing the Au/HA catalyst according to one embodiment of the present invention. As shown in FIG. 1B, in one embodiment, the Au/HA catalyst is synthesized by: immersing HA nanocrystals and gold trichloride trihydrate ($HAuCl_4.3H_2O$) in a liquid to form a mixture (step S112); stirring the mixture at a stirring temperature such that Au nanoparticles deposits on the HA nanocrystals (step S114); and drying the mixture at a drying temperature to obtain the Au/HA catalyst (step S116). In one embodiment, the liquid may be water. In one embodiment, the stirring temperature may be about 70-90° C., and the drying temperature may be about 100° C.

Figure 1C:
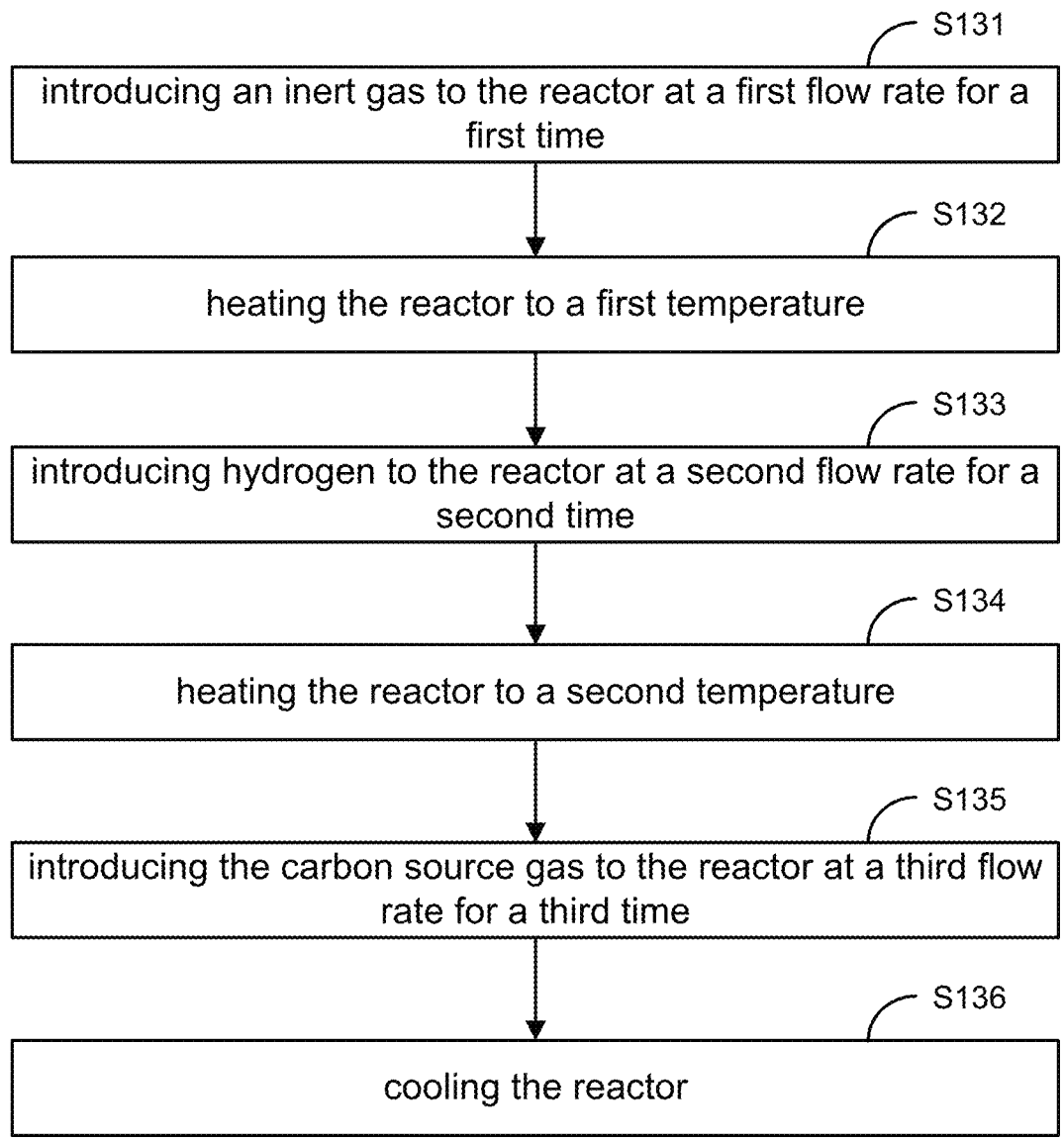
FIG. 1C shows a flowchart of heating the thin film with the carbon source gas according to one embodiment of the present invention.

FIG. 1C shows a flowchart of heating the thin film with the carbon source gas according to one embodiment of the present invention. As shown in FIG. 1C, in one embodiment, heating of the thin film with the carbon source gas includes: introducing an inert gas to the reactor at a first flow rate for a first time (step S131); heating the reactor to a first temperature (step S132); introducing hydrogen to the reactor at a second flow rate for a second time (step S133); heating the reactor to a second temperature (step S134); introducing the carbon source gas to the reactor at a third flow rate for a third time (step S135); and cooling the reactor (step S136).

In one embodiment, the inert gas includes Ar. In some embodiments, the first flow rate is about 150-600 ml/min, and the first period is about 5-20 minutes; the second flow rate is about 50-300 ml/min, and the second period is about 5-20 minutes; and the first temperature is about 400-600° C.

In one embodiment, the carbon source gas includes acetylene ($C_2H_2$). In a further embodiment, the second temperature is about 750-900° C., the third flow rate is about 5-30 ml/min, and the third time is about 15-90 minutes.

In one embodiment, the carbon source gas includes methane ($CH_4$). In a further embodiment, the second temperature is about 850-1000° C., the third flow rate is about 40-240 ml/min, and the third time is about 15-60 minutes.

Another aspect of the present invention relates to a multicomponent and biocompatible nanocomposite material. In one embodiment, the nanocomposite material includes a graphene structure formed with a plurality of graphene layers; and Au/HA nanoparticles distributed within the graphene structure. The nanocomposite material is formed by heating an Au/HA catalyst thin film with a carbon source gas to perform radio frequency chemical vapor deposition (RF-CVD), as described in the step S130 of FIG. 1A.

In one embodiment, the carbon source gas includes acetylene. In one embodiment, the carbon source gas includes methane.

In some embodiments, the nanocomposite material may be formed by the method as shown in FIG. 1A. In some embodiments, the Au/HA catalyst thin film may be formed by the synthesizing method as shown in FIG. 1B and the distributing step S120 of FIG. 1A. In some embodiments, the heating of the Au/HA catalyst thin film may be performed by the method as shown in FIG. 1C.

As described above, embodiments of the nanocomposite material and the synthesizing method may be used in a variety of applications, such as regeneration of bone tissues for the high bio-compatibility of the material. For example, one aspect of the present invention relates to a method of regenerating bone tissues. In one embodiment, the method includes: synthesizing a multicomponent and biocompatible nanocomposite material as disclosed in any of the above-mentioned embodiments, and applying the nanocomposite material in an area of bone regeneration. In some embodiments, other applications of the nanocomposite material and the synthesizing method may include coatings for various implantable devices, tissue regeneration, and other such suitable applications.

Example

In this example, the synthesis of the nanocomposite material (few-layer graphenes over a novel Au/hydroxyapatite catalytic system) was performed by RF-CVD, with acetylene and methane as the carbon source gases. The synthesis time was found to influence linearly the dimensions of the graphitic layers and asymptotically their corresponding thermal decomposition temperature. The resulting multicomponent nanocomposite material, formed out of graphene layers and Au nanoparticles supported on the surface of HA nanoparticles, was found to have good biocompatibility and induce excellent bone cellular proliferation. Such multicomponent nanocomposite materials could find excellent applications in the area of bone regeneration given the excellent biocompatibility, 3D structure, and unique composition.

Synthesis Conditions

The Au/HA catalyst in this example was prepared by homogeneous deposition-precipitation with urea. The Au target concentration was of about 1%. The preparation method and metal concentration were chosen such that a catalyst with very small (about 3-10 nm) and well-dispersed Au nanoparticles over the support is obtained.

In this example, the support (nanocrystals of HA) (Berkeley Advanced Biomaterials, Inc.) was immersed in water together with the corresponding quantity of $HAuCl_4.3H_2O$ (Merk) and urea (Merk) in excess. The mixture was vigorously stirred at about 80° C. over night. The final pH of the solution was found to be about 8.5. In these conditions, the slow generation of $OH^-$ groups by slow decomposition of urea ensures the precipitation and deposition of gold as small nanoparticles mainly on the support and not in solution. The resulting precipitate was thoroughly washed with water to remove the chlorine, dried in air at about 100° C. for 6 hours, and then calcined in air at about 250° C. for about 2 hours.

The few-layer graphene synthesis was done by RF-CVD, which has been presented previously and which allows high temperature heating rates of over 350° C./min [24, 25]. The synthesis reactor is composed of a water-cooled quartz tube which allows accurate control of the reaction conditions [11].

For the catalytic synthesis in this example, approximately 50 mg of Au/HA catalyst has been distributed into a thin film on the flat bottom of a graphite crucible, which was introduced in a horizontal quartz reactor (diameter about 30 mm and length about 50 cm) placed in the middle of a water-cooled inductive coil made out of a copper tube and connected to a high frequency generator (about 1.2 MHz, about 5 kW) [11].

The catalyst and the crucible in the closed reactor were washed in Ar at the first flow rate of about 300 ml/min for about 10 minutes as the first time. Then, the crucible was heated to the first temperature of about 500° C. in Ar. At this point, over Ar was also introduced a flow of $H_2$ at the second flow rate of about 100 ml/min that was maintained for about 10 min as the second time. The temperature was further increased to the second temperature of about 850° C. When $C_2H_2$ was used as the carbon source gas, the Ar was stopped, and, over the $H_2$ flow, $C_2H_2$ was introduced at the third flow rate of about 10 ml/min. The reaction time (the third time) was varied for about 10, 20, 30, 60, and 90 minutes, after which the $C_2H_2$ and $H_2$ flows were stopped. Then, Ar was re-introduced into the reactor, and the reactor was disconnected from the generator and allowed to cool down naturally.

Identically, when $CH_4$ was used as the carbon source gas, the second temperature was at about 950° C., the synthesis reactions were carried out with $CH_4$ being introduced at the third flow rate of about 80 ml/min, and the reaction time (the third time) was varied for about 30-60 minutes.

Throughout all of these reactions, the temperature was monitored and maintained constant by the use of an infrared thermometer (Impac, IGA 8 plus).

Analytical Characterization of Samples

The thorough structural and morphological characterization of the Au/HA catalyst and the resulting nanocomposite materials of Au/HA@graphene was performed by scanning and transmission electron microscopy (SEM-JSM-7000F and TEM-JEM-2100F, both JEOL Inc.), energy-dispersive X-Ray spectroscopy (EDS) (EDAX Inc.), thermogravimetrical analysis (TGA), and Raman spectroscopy. The total surface area ($S_t$) and pores volume ($V_p$) and size ($R_m$) for hydroxyapatite and Au/HA catalyst were calculated from $N_2$ adsorption-desorption isotherms at 77K, using BET method (for surface area) and Dollimore Heal method (for porosity). The isotherms were registered using a Sorptomatic 1990 instrument (Thermo Electron Corporation). Prior to analysis, the catalyst sample was degassed in vacuum (1 Pa) at about 150° C. for about 3 hours.

For the TEM analysis, the samples were homogeneously dispersed by sonication (about 30 minutes) in 2-propanol. A few drops of the suspensions were placed on the TEM grid, dried, and analyzed. Au/HA catalysts were imaged at about 200 kV both in TEM and STEM modes. STEM images were collected in HAAD mode to detect Au nanoparticle shapes. Distribution of EDS spectra were often collected along with the HAAD STEM images to produce elemental mappings. The EDS elemental maps can be overlaid on the STEM images to confirm the existence of Au nanoparticles. All graphenes images and electron diffraction patterns were collected at about 80 kV.

The Raman spectra were collected at room temperature by using a JASCO type NRS 3300 spectrophotometer in a backscattering geometry coupled to a CCD (−69° C.) detector with an about 600 $mm^{-1}$ grid and a spectral resolution of about 1.45 $cm^{-1}$. The incident laser beam with a diameter of 1 $\mu m^2$ was focused through an Olympus microscope (100× objective), and the calibration was made by using the Si peak at about 521 $cm^{-1}$. The excitation was done by using an Ar-ion laser with a wavelength of 514 nm and a power at the sample surface of about 4.5 mW.

The thermogravimetric analysis was performed using a SDT Q 600 (TA Instruments) instrument in air flow (about 100 mL/min) for the temperature range of about 25-750° C. and with a heating rate of about 5° C./min.

Osteoblastic Cell Cultures Incubation

The murine calvaria-derived MC3T3-E1 osteoblast-like cells were obtained from the American Type Culture Collection (ATCC) and maintained using established procedures. Cells were normally grown in about 75 $cm^2$ flasks ($10^6$ cells) with phenol red free alpha-modified minimum essential medium containing 10% fetal bovine serum (FBS), about 1% penicillin (about 500 units/ml), and streptomycin (500 units/ml) at about 37° C. in an about 5% $CO_2$ atmosphere for about 7 days prior to seed coating. The cells were kept in aseptic conditions, and the medium was changed about every 2 days. Cells were seeded in about 35 mm tissue culture dishes and over Au/Ha@graphene-coated identical culture dishes, in both cases at a density of about $25 \times 10^4$ cells/dish. The cells were incubated for up to about 6 days. For microscopy evaluation, the cells were washed thoroughly with about 10 mM phosphate buffered saline (PBS, pH 7.4) three times and fixed with about 10% formaldehyde solution for about 10 min, washed three times with PBS and stained with ethidium bromide-acridine orange fluorescent dye. The cells were observed under UV light by light transmission microscopy using an Olympus BX 51 microscope.

Osteoblastic Cell SEM Samples Preparation

Cell samples that were grown for about 24 hours over the HA/graphene substrates were first fixed with about 3% glutaraldehyde and secondly with about 2% osmium tetraoxide. After dehydration with an increasing graded ethanol series, the cells were dried using a critical point dryer Samdri®-PVT-3D, Tousimis Research Corporation. The dried samples were coated with a few nm layer of gold by sputtering and were mounted on SEM aluminum stubs using carbon double-sided tape. High resolution images were obtained using filed emission Scanning Electron Microscopy SEM (JSM-7000F) with accelerating voltage about 15 kV and a working distance of about 10 mm.

MTT Based Cytotoxicity Assay

The assay (CytoSelect™ Cell Viability and Cytotoxicity Assay kit, USA) is based on scrutinizing the ability of living cells to metabolize a water-soluble tetrazolium yellow dye 3-(4,5-dimethylthiazol-2-yl)-2,5-diphenyl tetrazolium bromide (MTT) into an insoluble purple formazan salt. The metabolic activity of the cell is proportional to the color density formed. The cells were seeded in 96 well plates at a density of about $5 \times 10^4$ cells/well. Growth medium was used as a negative control. The provided cytotoxic saponine solution was used as a positive control. The Au/HA@graphene nanocomposite materials were incubated at concentrations of about 0.1, 1, 10, and 50 µg/ml with the cells. Prior to incubation, the cells were washed twice with fresh cold culture media. About 100 µl fresh medium was added with about 10 µl of MTT reagent to each well, and the cells were incubated overnight at about 37° C. Once the purple precipitation was clearly visible in each well, about 100 µl of detergent solution was added to each well; the plates were covered, and the cells were incubated for 4 hours in the dark. The absorbance of each sample at about 570 nm was measured by using a microtiter plate reader (BioRad, iMark, USA).

Lactase Dehydrogenase (LDH) Release

Lactase dehydrogenase release was measured using the LDH assay kit (Cayman Chemicals, Ann Arbor, Mich., USA) to evaluate the cell membrane integrity. Released LDH in culture supernatants was measured with a coupled enzymatic assay that results in the conversion of a reduced tetrazolium salt (INT) into a highly colored formazan product which absorbs strongly at about 490 nm. MC3T-E1 cells were seeded in a 96-well plate at a density of (about $5 \times 10^4$ cells) and treated with different concentrations of Au/HA@graphene nanocomposite materials (about 0.1, 1, 10, and 50 µg/ml) freshly dispersed in culture medium and incubated for about 24 hours. Next, about 120 µl of supernatant was transferred into about 1.5 ml tubes and centrifuged for 5 minutes at about 400 g. About 100 µl of the supernatant was transferred to new 96-well plates, followed by the addition of about 100 µl of LDH reaction solution. The plate was incubated for about 30 minutes at room temperature on the orbital shaker. Absorbance was recorded at 490 nm using a microplate reader for colorimetric detection (BioRad, iMark, USA).

Synthesis and Characterization of the Au/HA@Graphene Nanostructures

The $N_2$ adsorption-desorption isotherms registered at 77K for HA and Au/HA catalysts are of type II, specific to mezoporous solids. Size distribution of the pores is very large and situated in the middle portion of the mezoporous domain [26]. Table 1 presents the total surface area ($S_t$), pores volume ($V_p$), and size ($R_m$) for both the hydroxyapatite support and the Au/HA catalyst. As shown in Table 1, the surface area and porosity values of Au/HA catalysts are very close to the values measured for HA, proving that the textural characteristics of the material were not damaged in the catalyst preparation process.

TABLE 1

The total surface area ($S_t$), pores volume ($V_p$) and size ($R_m$) for HA and Au/HA catalyst

| Nr. | Sample | $S_t$ (m²/g) | $V_p$ (cm³/g) | $R_m$ (Å) |
|---|---|---|---|---|
| 1 | HA | 35 | 0.06 | 131-176 |
| 2 | Au/HA | 34 | 0.07 | 152-176 |

Figure 2:
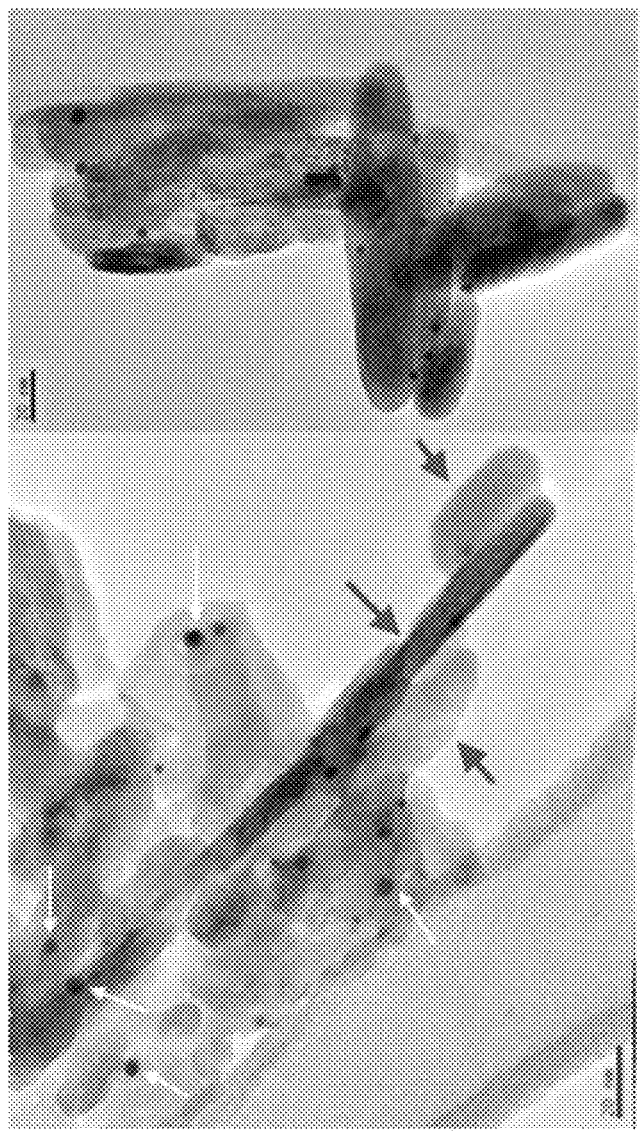
FIG. 2 shows TEM micrographs of the Au/HA catalyst collected at about 200 kV according to one embodiment of the present invention.

FIG. 2 shows TEM micrographs of the Au/HA catalyst collected at about 200 kV according to one embodiment of the present invention. In FIG. 2, the TEM images are presented for the Au/HA catalyst after the calcination. As shown in FIG. 2, it can be observed that the Au/HA catalyst has a granular structure, formed of nanocrystals with elongated morphologies, similar to findings presented in previous reports [27].

The presence of such granular structures (marked with red arrows) is clearly evident in the TEM analysis of the Au/HA catalyst. A granule with a diameter of about 20 nm and a length of 45 nm along and another with a diameter of about 10 nm and a length of about 200 nm is shown in FIG. 2. Such elongated granules with a diameter between about 10-20 nm and lengths of about 100-200 nm have also been observed in other TEM images of the catalyst. Also visible is the presence of dark spherical clusters (marked with white arrows) distributed over the entire surface of the catalyst and EDS studies indicated that these morphologies are the Au nanoparticles deposited over the surface of the HA structures.

Figure 3:
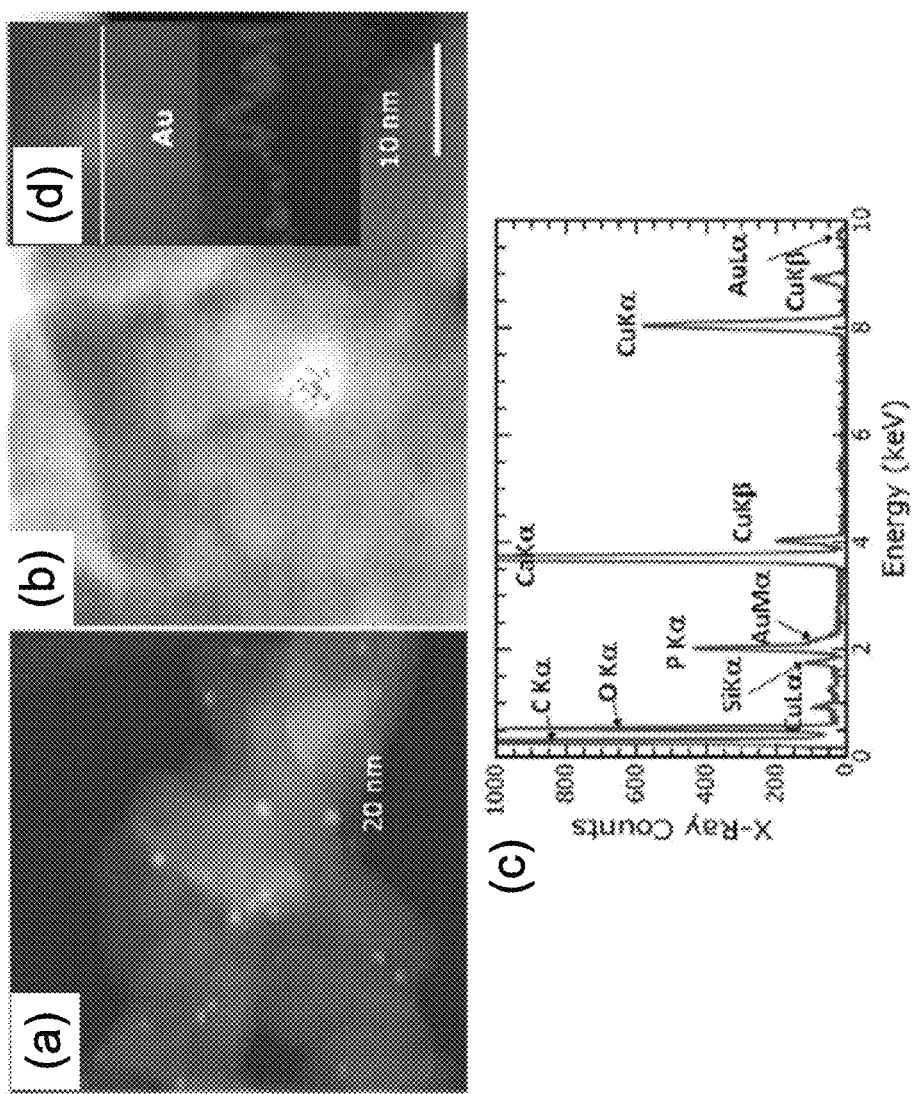
FIG. 3 shows the Au/HA catalyst collected at about 200 kV according to one embodiment of the present invention, where (a) shows HAAD STEM (about 200 kV) images of Au/HA catalyst; (b) shows a nanoparticle with Au EDS X-ray signal overlay (dots); (c) shows a EDS X-ray spectrum from the imaged region of Au/HA given in (a); and (d) shows a EDS line scan over the nanoparticle shown in (b) (top) and the Au signal distribution (bottom).

FIG. 3 shows the Au/HA catalyst collected at about 200 kV according to one embodiment of the present invention, where (a) shows HAAD STEM (about 200 kV) images of Au/HA catalyst; (b) shows a nanoparticle with Au EDS X-ray signal overlay (dots); (c) shows a EDS X-ray spectrum from the imaged region of Au/HA given in (a); and (d) shows a EDS line scan over the nanoparticle shown in (b) (top) and the Au signal distribution (bottom).

As shown in FIG. 3, HAAD images of the Au(1%)/HA catalyst with 1% Au obtained in STEM mode along with EDS analysis. In the STEM HAAD images as shown in figure (a), elements with higher atomic numbers appear brighter while those with lower atomic numbers appear darker, which clearly shows the uniform size distribution of the catalyst Au nanoparticles. These nanoparticles have slightly elliptic shapes with average minor and major dimensions of about 3.6±0.5 nm and about 4.1±0.5 nm, respectively.

To confirm that these particles are indeed Au nanoparticles, two-dimensional mappings and line scans in EDS mode were carried out. As shown in figure (b) of FIG. 3, a slightly higher magnification HAAD image of a single Au nanoparticle present on the surface of the HA catalyst is shown along with the EDS elemental mapping of the Au-specific X-ray signal overlaid (as dots). Figure (c) shows the EDS spectrum collected while capturing this set of image and elemental mapping. Au is clearly present along with Ca, O, and P, which are the major components of HA, even though the Au peaks are not as large as these other components since Au content is only about 1%. The Au peak (shoulder) which is close to P line can be clearly recognized in figure (c). Cu and C signals come from the carbon film coated Cu TEM grid which was used to support the catalyst specimen in the TEM image.

In figure (d) of FIG. 3, an EDS line scan across this bright nanoparticle, as shown in figure (b), also proves it to be a Au nanoparticle. Au L-α X-ray peak intensity variation along the white line shown in figure (d) is plotted on the bottom matching the profile of this bright particle. These results clearly show that the bright particles shown in the HAAD images are undoubtedly Au nanoparticles, which are the catalytically active clusters responsible for the growth of graphenes in the CVD experiments.

Figure 4:
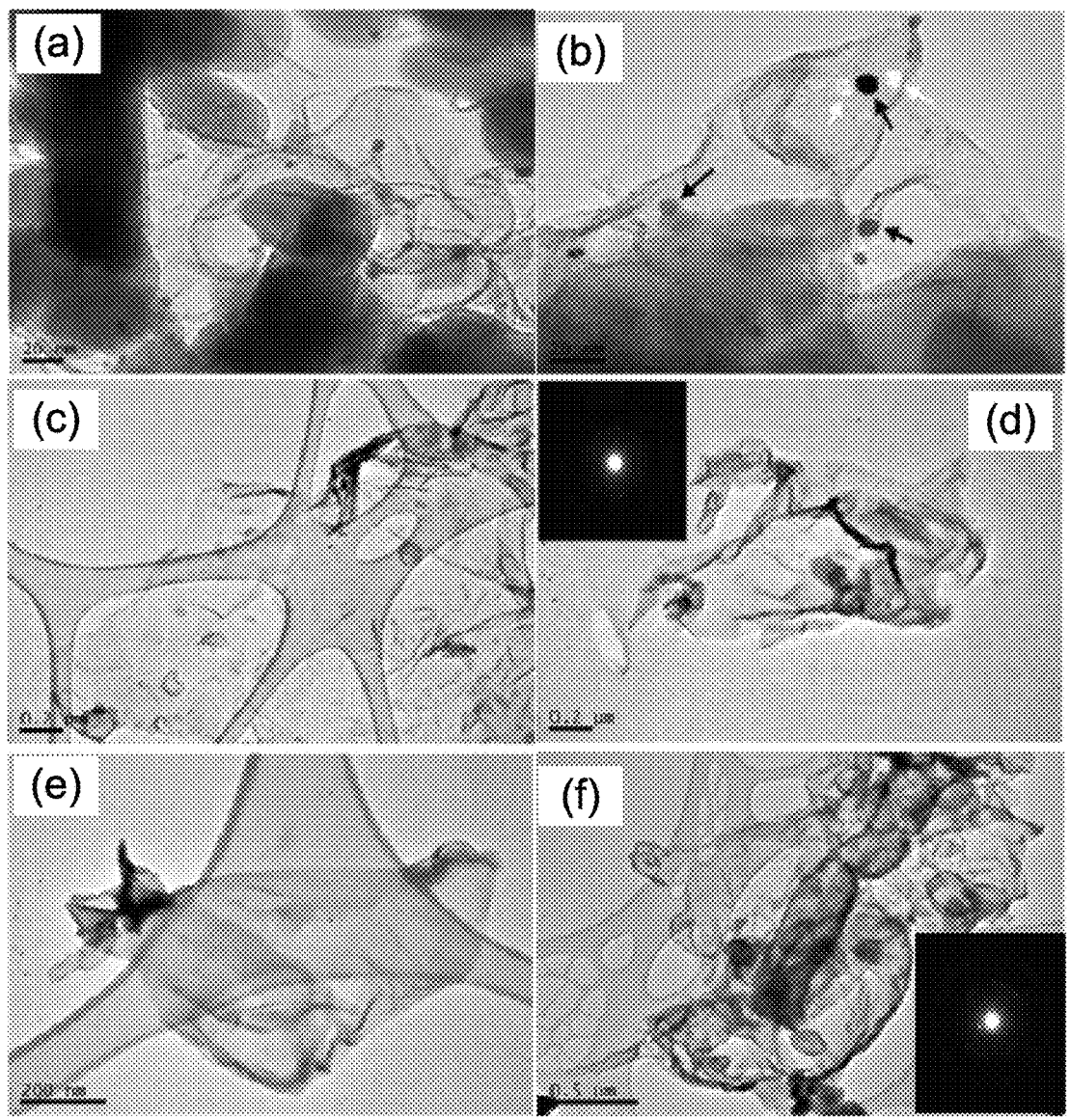
FIG. 4 shows TEM images (about 80 kV) for the few-layer graphene structures synthesized according to embodiments of the present invention, over the Au/HA catalysts out of acetylene for the different synthesis time according to embodiments of the present invention, where (a) and (b) show the nanocomposite material structures synthesized over the Au/HA catalysts out of acetylene for the synthesis time of about 30 minutes; (c) and (d) show the nanocomposite material structures synthesized over the Au/HA catalysts out of acetylene for the synthesis time of about 60 minutes; (e) shows the nanocomposite material structures synthesized over the Au/HA catalysts out of acetylene for the synthesis time of about 90 minutes; and (f) shows the nanocomposite material structures synthesized over the Au/HA catalysts out of $CH_4$ for the synthesis time of about 30 minutes.

FIG. 4 shows TEM images (about 80 kV) for the few-layer graphene structures synthesized according to embodiments of the present invention, over the Au/HA catalysts out of acetylene for the different synthesis time according to embodiments of the present invention, where (a) and (b) show the nanocomposite material structures synthesized over the Au/HA catalysts out of acetylene for the synthesis time of about 30 minutes; (c) and (d) show the nanocomposite material structures synthesized over the Au/HA catalysts out of acetylene for the synthesis time of about 60 minutes; (e) shows the nanocomposite material structures synthesized over the Au/HA catalysts out of acetylene for the synthesis time of about 90 minutes; and (f) shows the nanocomposite material structures synthesized over the Au/HA catalysts out of $CH_4$ for the synthesis time of about 30 minutes.

In FIG. 4, the TEM images show the carbonaceous structures synthesized over the Au/HA catalyst with about 1% Au out of acetylene or methane. These TEM images indicate that the resulting carbonaceous nanostructures for both $C_2H_2$ and $CH_4$ were few-layer graphenes. Since no additional purification was performed on any of these products, the nanocomposite materials are referred to as Au/HA@graphene composites. It should be noted that the dimension of the graphitic layers increased with the reaction time. The same observation was also made previously when graphene layers were synthesized on a Fe:Co:MgO catalyst [28].

For about 10 min of reaction time, the TEM analysis did not indicate the presence of well-defined graphenes sheets, and for about 20 min reaction time, these graphitic layers are very rare and with dimensions of about 50-70 nm (not shown here). Beyond about 30 minutes of synthesis, they are well-structured with dimensions of about 100-150 nm, as shown in figures (a) and (b) of FIG. 4, while for about 60 min, as shown in figures (c) and (d), and for about 90 min, as shown in figure (e), the graphitic layers had dimensions of about 1-1.5 μm. Figures (a) and (b) also show Au nanoparticles (black circular structures) that were lifted off the support and moved during the growth of the carbonaceous structures (marked with black arrows). Their dimensions range between 3 and 6 nm. Such nanostructures have been observed in all of the images of the structures obtained for various synthesis conditions. The white arrows in figure (b) indicate defects in the circular shape of the graphitic layers. The inset of figure (d) presents the electron diffraction pattern obtained for the few-layer graphene structures indicating their high crystallinity and the fact that the structures are composed of a small number of layers.

In figure (f) of FIG. 4, the TEM image shows the graphitic layers obtained out of $CH_4$ with about 30 minutes of reaction time, and the inset shows the corresponding electron diffraction pattern. The graphene structures obtained from $CH_4$ are polycrystalline and have dimensions in the order of micrometers, but have lower density over the catalyst as compared to the case when $C_2H_2$ was used as the carbon source. The same observations were made for the reaction time of about 60 minutes. As the synthesis time further increased past about 90 minutes for $C_2H_2$ and past about 60 minutes for $CH_4$, respectively, the formation of a few nanofibers was observed, which is the reason that all of the reactions were stopped after about 60 minutes.

Figure 5:
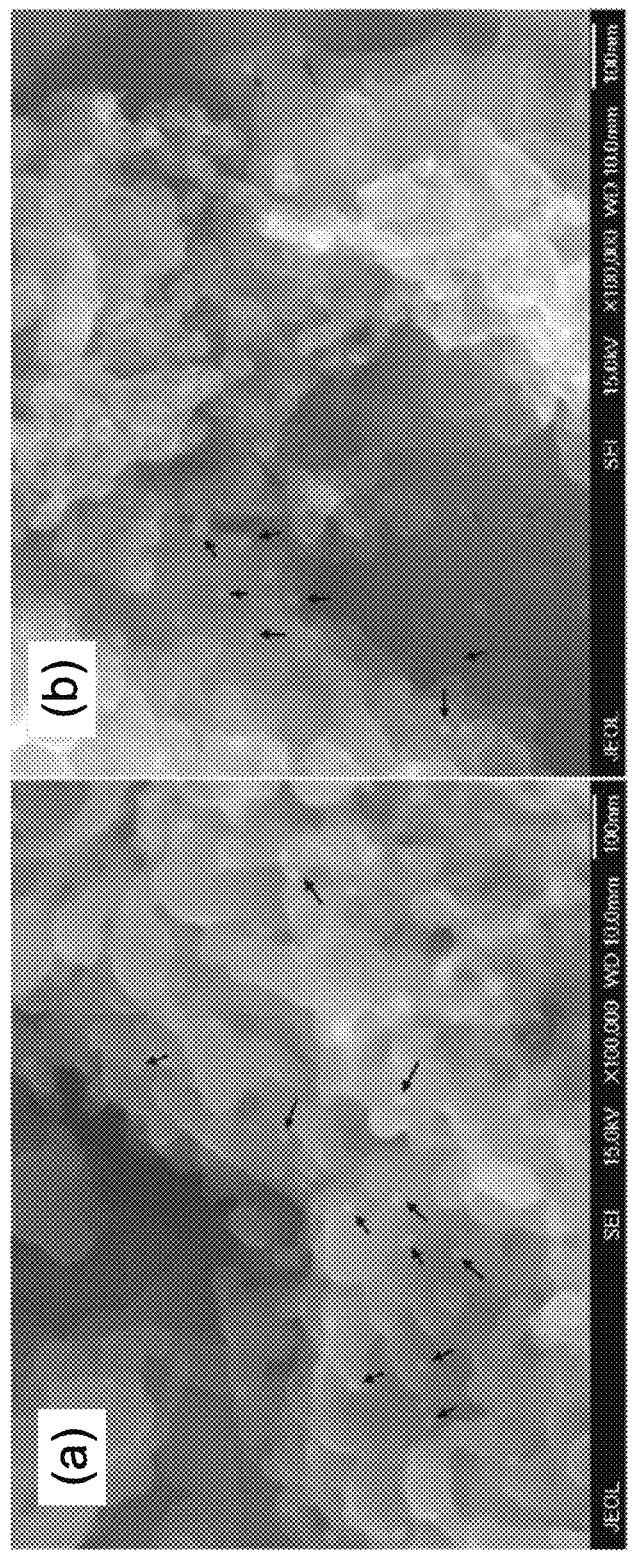
FIG. 5 shows SEM images of the nanocomposite material according to embodiments of the present invention, where (a) shows the nanocomposite material corresponding to about 30 minutes reaction time for $C_2H_2$, and (b) shows the nanocomposite material corresponding to about 60 minutes for $CH_4$, respectively.

FIG. 5 shows SEM images of the nanocomposite material according to embodiments of the present invention, where (a) shows the nanocomposite material corresponding to about 30 minutes reaction time for $C_2H_2$, and (b) shows the nanocomposite material corresponding to about 60 minutes for $CH_4$, respectively.

As shown in FIG. 5, the SEM images show that all of these nanocomposite materials were found to have a flattened structure with rounded edges. As supported by the TEM analysis, the presence of clusters corresponding to the Au nanoparticles that are incased in the graphitic layers with dimensions of around 10 nm is also shown in the SEM images (marked with darker and lighter arrows).

Figure 6:
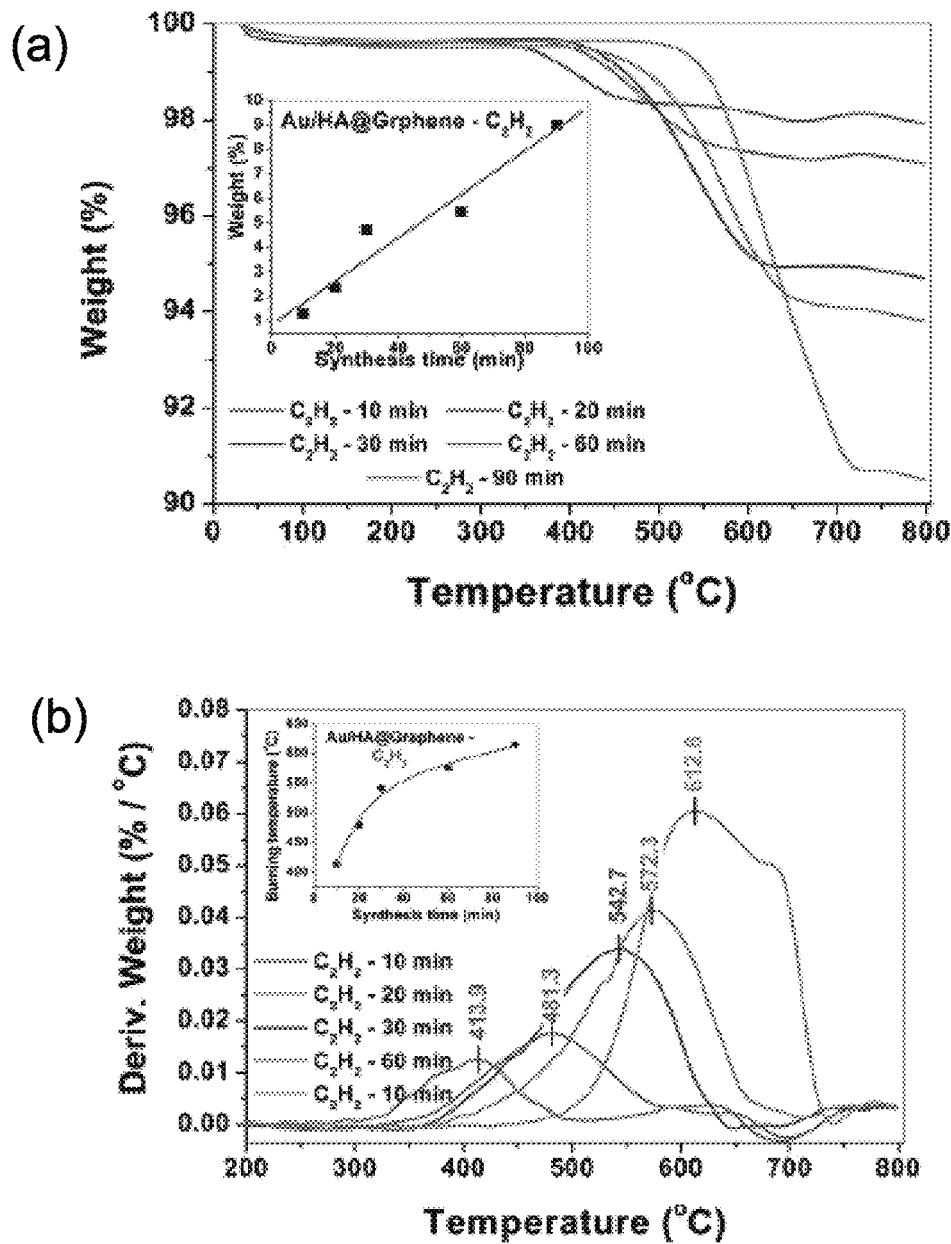
FIG. 6 shows charts for the nanocomposite materials synthesized out of acetylene according to embodiments of the present invention, where (a) shows a TGA chart of the variation of the graphitic mass as a function of the synthesis time, and (b) shows the corresponding DTA curves of the variation of the decomposition temperature of the graphitic materials as a function of the synthesis time.

FIG. 6 shows charts for the nanocomposite materials synthesized out of acetylene according to embodiments of the present invention, where (a) shows a TGA chart of the variation of the graphitic mass as a function of the synthesis time, and (b) shows the corresponding DTA curves of the variation of the decomposition temperature of the graphitic materials as a function of the synthesis time.

As shown in FIG. 6, the presence of a single profile of mass loss of the carbonaceous compound Au/HA@Graphene which was formed during the catalytic reactions may be observed. This observation is evident for longer times of synthesis. The inset of figure (a) of FIG. 6 presents the variation in the mass of the graphitic layers that were synthesized over the Au/HA catalysts as a function of the reaction time, indicating an almost linear relationship of these parameters. The DTA curves as shown in figure (b) give information on the thermal decomposition temperature—given by the position of the maximum peak relative to the temperature axis of the graphene layers present in the Au/HA@Graphene composites [29, 30].

This decomposition temperature grows asymptotic for the Au/HA@graphene structures with the synthesis time, possibly due to the increase in the dimensionality and crystallinity of the graphene layers, as was also observed by the TEM analysis. Furthermore, no mass decrease was observed for the temperature range of about 300-400° C., which corresponds to the non-crystalline or amorphous carbon decomposition, indicating the presence of only crystalline graphitic structures in the Au/HA@graphene composites [31, 32].

Figure 7:
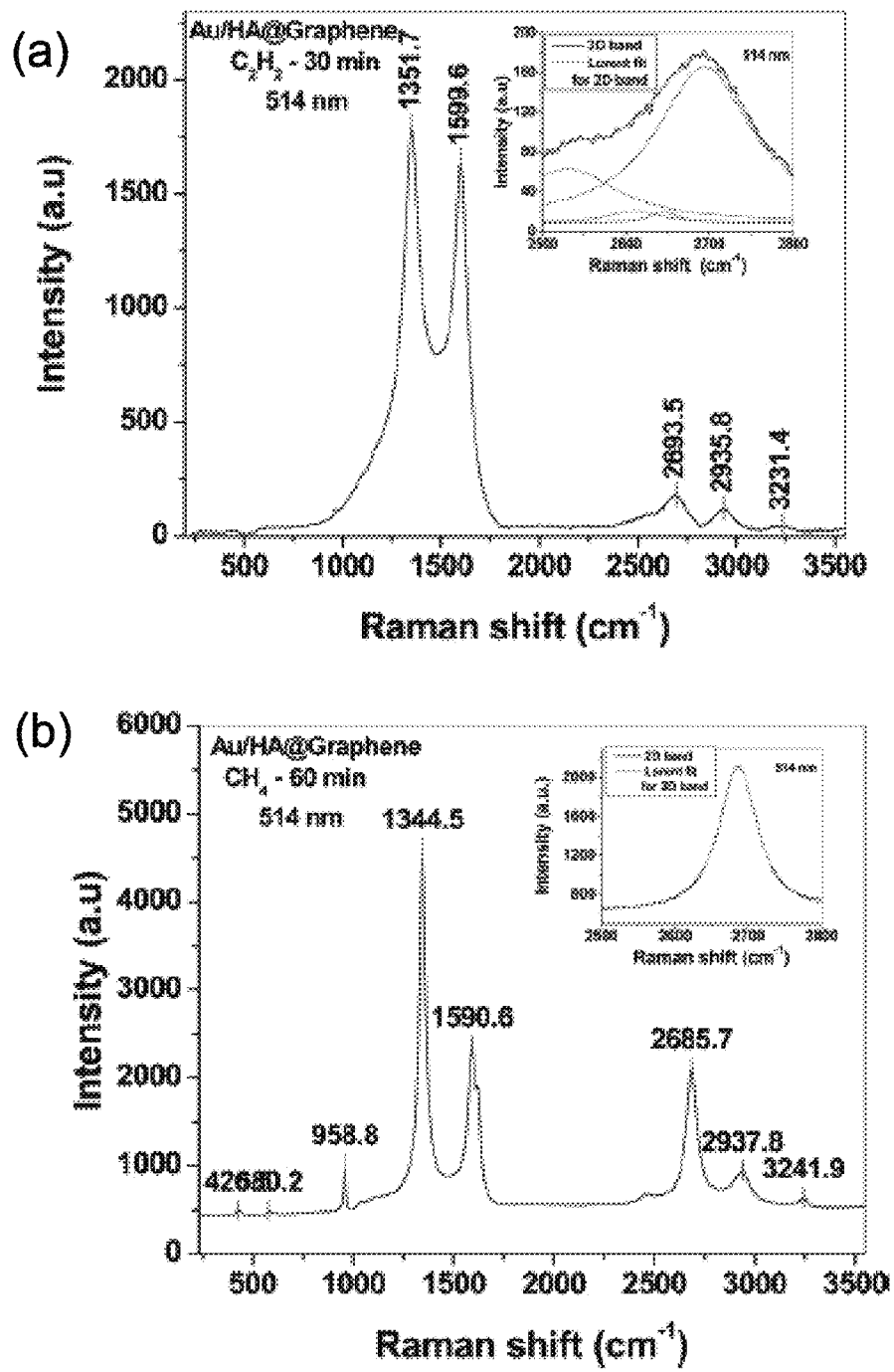
FIG. 7 shows Raman spectrum images for the nanocomposite materials according to embodiments of the present invention, where (a) shows the nanocomposite materials synthesized out of $C_2H_2$ for 30 minutes, and (b) shows the nanocomposite materials synthesized out of $CH_4$ for 60 minutes. The insets of the figures show the deconvolution of the 2D band into the corresponding Lorentzian curves according to one embodiment of the present invention.

FIG. 7 shows Raman spectrum images for the nanocomposite materials according to embodiments of the present invention, where (a) shows the nanocomposite materials synthesized out of $C_2H_2$ for about 30 minutes, and (b) shows the nanocomposite materials synthesized out of $CH_4$ for about 60 minutes. The insets of the figures show the deconvolution of the 2D band into the corresponding Lorentzian curves according to one embodiment of the present invention.

The TGA analysis for the structures synthesized out of $CH_4$ indicated the presence of significantly smaller amounts of graphene layers: about 0.3% and 0.5% for 30 and 60 min synthesis time, respectively. As shown in FIG. 7, the inset for each figure shows the decomposition of the 2D band into Lorentzian curves.

The Raman spectra of these structures indicate the presence of graphitic layers and are characteristic of graphenes with structural defects or damaged graphenes [33, 34]. It has been shown [33, 35, 36] that the shape of the 2D band (second order harmonic of the D band) positioned in the spectral domain of about 2500-2800 $cm^{-1}$ is strongly dependent upon the number of graphitic layers composing the few-layer graphene structures. In conformity with the published literature, the analysis of the 2D bands indicates the presence of four Lorentzian curves for the Au/HA@graphene synthesized out of $C_2H_2$, and of one to two for those synthesized out of $CH_4$. These studies further show the presence of only few-layer of graphenes in the nanocomposite material structures. The peaks situated at about 426, 580.2, and 958.8 $cm^{-1}$ in the spectrum as shown in figure (b) of FIG. 7 correspond to the HA [37]. The fact that these peaks are only present for the composites grown from $CH_4$ further shows the small amount of graphitic structures synthesized in these conditions over the Au/HA catalyst, which is in good agreement with the TEM and TGA studies.

Osteoblast Cells Proliferation Over Au/HA@Graphene Films

Figure 8:
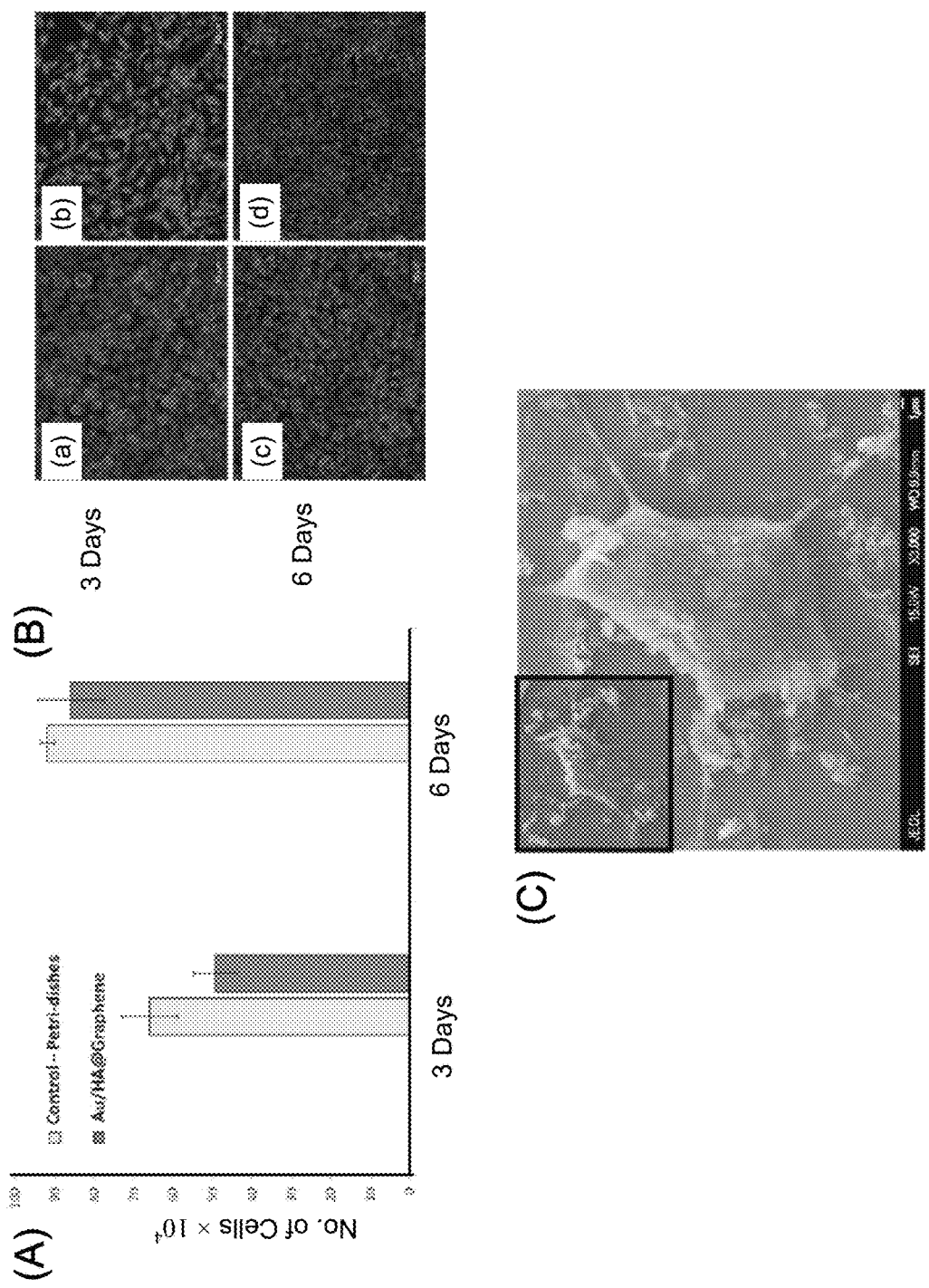
FIG. 8 shows cellular proliferation charts and images of nanocomposite material films composed of the nanocomposites grown with $C_2H_2$ as the carbon source gas for about 90 minutes according to one embodiment of the present invention, where (A) shows a chart of cellular proliferation analysis of the cells incubated at a density of about $2\times10^5/35$ mm tissue culture petri dishes (control) and over Au/HA@graphene films coating polymeric petri dishes; (B) shows representative photomicrograph images of the bone osteoblastic cells (MC3T3) incubated over control about 35 mm polysterene tissue culture dishes for (a) about 3 days and (c) about 6 days (c), and over Au/HA@Graphene films for (b) about 3 days and (d) about 6 days; and (C) shows a SEM image of the osteoblast cells growing over the Au/HA@graphene nanocomposite materials according to one embodiment of the present invention.

FIG. 8 shows cellular proliferation charts and images of nanocomposite material films composed of the nanocomposites grown with $C_2H_2$ as the carbon source gas for about 90 minutes according to one embodiment of the present invention, where (A) shows a chart of cellular proliferation analysis of the cells incubated at a density of about $2\times10^5/35$ mm tissue culture petri dishes (control) and over Au/HA@graphene films coating polymeric petri dishes; (B) shows representative photomicrograph images of the bone osteoblastic cells (MC3T3) incubated over control about 35 mm polysterene tissue culture dishes for (a) about 3 days and (c) about 6 days (c), and over Au/HA@Graphene films for (b) about 3 days and (d) about 6 days; and (C) shows a SEM image of the osteoblast cells growing over the Au/HA@graphene nanocomposite materials according to one embodiment of the present invention.

Nanostructural materials have proved to be excellent candidates as components in multifunctional coatings for implantable devices to promote higher cellular differentiation and proliferation [38]. The primary properties that these nanomaterials must have in order to be successfully used in bio-medical applications are good biocompatibility, high stability in biological environments, high ability of allowing cells to proliferate and differentiate, and low toxicity. The Au/HA@graphene nanocomposite materials have tremendous potential for use as multicomponent materials in bone regeneration applications, especially given that HA is a natural component of the bone, Au nanoparticles have low cytotoxicity, and the few-layer graphene structures offer the 2D morphology that is required for the cells to proliferate. To study the ability of these materials to interact with bone cells, films of Au/HA@graphene were sprayed over the surface of culture petri dishes, and murine calvaria-derived MC3T3-E1 osteoblast-like cells were cultured over these films at a concentration of about $25\times10^4$ cells/dish. The proliferation of the cells over the resulting films was investigated and compared to the uncoated petridishes for about 3 and 6 incubation days. The results of these experiments are shown in FIG. 8.

As shown in figures (A) and (B) of FIG. 8, the cells were incubated at a density of about $2\times10^5/35$ mm tissue culture petri dishes (control) and over Au/HA@graphene films coating polymeric petri dishes. The cells were incubated for about 3 and 6 days, and the medium was changed about every 48 hours. Three separate experiments were performed for each data point. The cellular proliferation over the Au/HA@graphene nanocomposite thin films was found to be statistically similar to the one over the control petri dish substrates. A slightly smaller number of cells was observed for the controls after about 3 days of incubation, but, for about 6 days, the difference in the number of cells growing on the control and the Au/HA@graphene films became almost identical.

Given these findings, the Au/HA@graphene composite materials could find excellent possible applications as coatings for various implantable devices to increase their osseointegration and to limit their rejection. To exemplify, the inventors have presented that the same murine calvaria-derived MC3T3-E1 osteoblast-like cells had significantly lower proliferation rates as a function of time when incubated in identical conditions over $TiO_2$ substrates as compared to the Au/HA@graphene nanocomposites [39]. In this study, the cells were plated initially at a density of about $10^4$/well, and, after about 7 days of incubation, their density over the $TiO_2$ nanotubular substrates was found to be approximately $5\times10^4$ as compared to about $15\times10^4$ for the petri dish controls.

As shown in figure (C) of FIG. 8, the SEM studies clearly indicate that the osteoblast cells have a high ability to grow over the Au/HA@graphene films without any observable variation in their morphology or size. These findings indicate that the nanocomposite materials do not seem to induce undesired cellular toxic effects. It can be concluded that the use of individual components with low toxicity in the Au/HA@graphene composite structure, such as gold nanoparticles deposited on the HA support as the biocompatible functional component and few-layer graphene structures, do not seem to significantly alter the morphology of the cells or to hinder the cellular proliferation and to have limited undesired cytotoxic effects.

Figure 9:
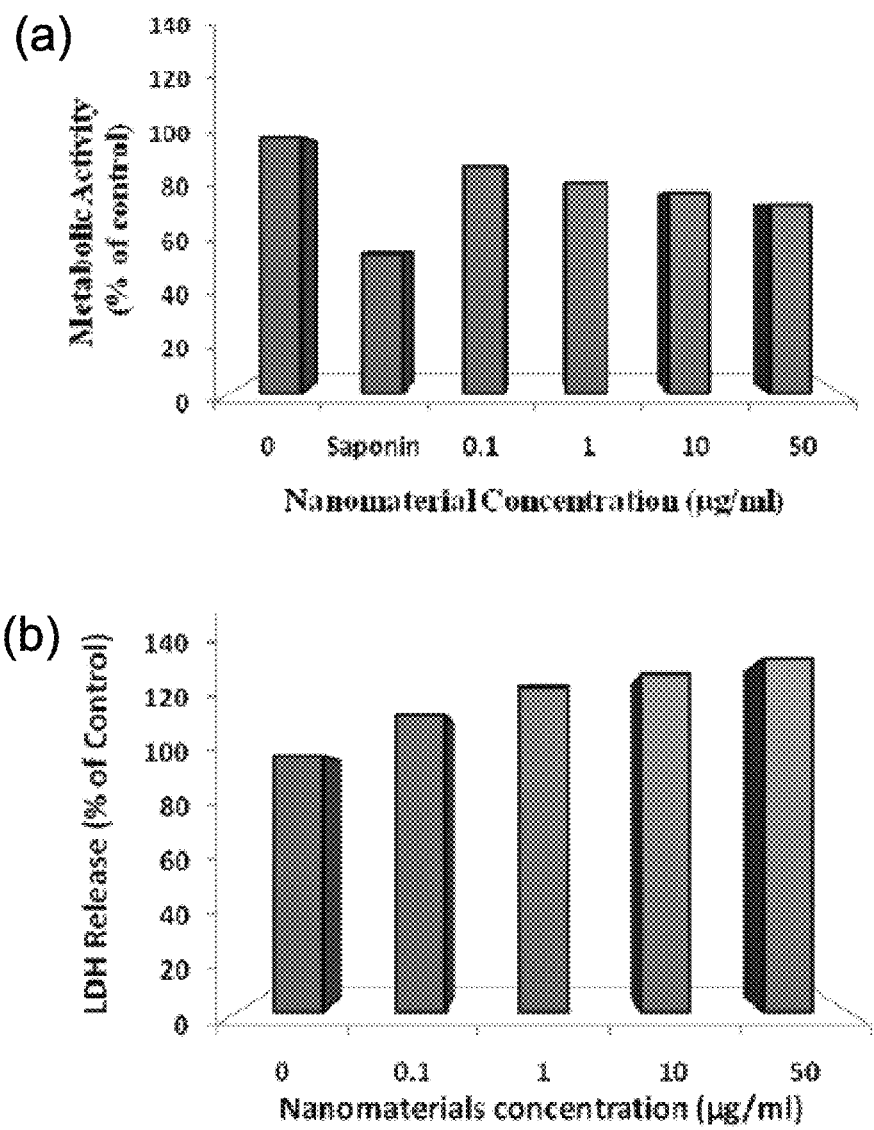
FIG. 9 shows charts of studies for the MC3T3-E1 bone cells when incubated for about 24 hours with the nanocomposite materials in various concentrations according to embodiments of the present invention, where (a) shows MTT studies, and (b) shows LDH release studies. For the MTT studies, saponin was used as a positive control. All studies were done in triplicates according to one embodiment of the present invention.

FIG. 9 shows charts of studies for the MC3T3-E1 bone cells when incubated for 24 hours with the nanocomposite materials in various concentrations according to embodiments of the present invention, where (a) shows MTT studies, and (b) shows LDH release studies. For the MTT studies, saponin was used as a positive control. All studies were done in triplicates according to one embodiment of the present invention.

One of the major concerns in using nanomaterials for various bio-medical applications is their potential toxicity and ability to induce undesired effects when in contact with various cell lines. The toxicity of carbonaceous nanostructures has been previously shown to be both shape- and concentration-dependent [23]. To further understand the potential toxicity of the Au/HA@graphene nanocomposite materials to the murine calvaria-derived MC3T3-E1 osteoblast-like cells, they were dispersed in cell medium at concentrations of about 0.1, 1, 10, and 50 µg/ml and incubated with the cells for about 24 hours. Commonly used MTT and LDH release studies were performed, and the results are shown in FIG. 9.

MTT assay is a commonly used method to understand the possible negative effects that nanomaterials induce in cells by quantifying the cellular mitochondria activity when exposed to the nanomaterials. As shown in figure (a) of FIG. 8, after 24 hours of incubation with the Au/HA@graphene nanocomposite materials, the metabolic activity of the cells was found to be, as expected, concentration-dependent, but the overall variations were relatively small. The results indicate that, at higher concentrations, the Au/HA@graphene induce a more intense toxic response as compared to lower concentrations. An interesting finding is that, for all concentration values of up to 50 µg/ml (highest concentration investigated), the decrease in the metabolic activity of the MC3T3-E1 cells was significantly smaller compared to that observed for graphene-only nanostructures, as reported in [23]. This indicates a possibly lower toxicity of Au/HA@Graphene nanocomposite materials compared to the few-layer graphene structures alone. Graphene and Au/HA@Graphene nanocomposite materials are expected to have dissimilar interactions with the cells, given the variations in dimension, shape, surface chemistry, and their variable ability to agglomerate on the cellular membranes.

To further understand the cytotoxic effects induced by the Au/HA@graphene structures to the bone MC3T3-E1 cells, lactate dehydrogenase (LDH) release was analyzed in order to evaluate the cellular membrane damage, which is considered a necrosis marker. Similar to the MTT studies, the LDH release values also showed a concentration-dependent trend with the highest values corresponding to the higher concentrations of nanomaterials. These values are again in excellent correlation with the previously reported values for LDH release for graphene materials exposed to PC 12 cells [23] but are significantly lower than those measured for single-walled carbon nanotubes. These studies clearly indicate that the Au/HA@graphene nanocomposite materials have a high biocompatibility with the MC3T3-E1 bone cells and could be the foundation for multifunctional technologies in the bone and tissue regeneration field. The presence of the Au nanoparticles within the graphitic structure of the few-layer graphenes (as shown in FIG. 5) is not believed to play a major role in the overall toxicity of the composites, even in the case of becoming free from the crystalline structures of the sheets. Toxicity evaluation assays (such as those presented in FIGS. 8 and 9) have shown that Au nanoparticles with a concentration of up to about 150 µg/ml did not induce any significant cytotoxic effects in the MC3T3-E1 bone cells (data not presented here). Therefore, the combination of the graphene sheets with Au nanoparticles will form as a multifunctional nanocomposite with low undesired cytotoxic effects and therefore major potential applications in nanomedicine. Moreover, the presence of carbon graphene structures that can be easily functionalized with various bio-molecules, including growth factors, proteins, or drugs, gives these materials great potential in the development of novel functional scaffolds in stem cell biology for fast tissue formation.

In sum, the analysis demonstrated the ability of a new catalytic system Au/HA (with 1% Au) to generate few-layer graphene structures by RF-CVD with acetylene or methane as the carbon sources. The surface area and pores analysis did not indicate major variations between the HA and Au/HA structures, indicating no major structural or surface changes induced by the addition of the Au catalytic nanoclusters. The electron microscopy indicated the presence of Au nanoclusters arranged uniformly over the surface of the HA particles with diameters between about 2 and 7 nm. The catalyst was found to produce graphitic layers with dimensions and morphologies that depended upon the growth conditions. The dimension of the graphitic layers was found to increase with the synthesis time. Also the mass of the graphene layers was found to grow linearly with the reaction time, while the thermal decomposition temperature increases asymptotically. Raman analysis and the deconvolution of the 2D band indicated the presence of graphitic materials with only a few graphene layers but with possible structural defects. These structures were found to have good biocompatibility towards the bone cells' proliferation and growth. Moreover, the MTT and LDH release assays indicated that the Au/HA@graphene multicomponent nanocomposite materials have a very low toxic effect, but one that is dose-dependent, when exposed to the MC3T3-E1 bone cells. Such complex nanostructural systems could be the foundation for the formation of highly active scaffolds for tissue and bone regeneration and formation.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

REFERENCE LIST

[1] Yoshikawa, H.; Myoui, A. *J. Art Organ* 2005, 8, 131-136.
[2] Yeong W-Y.; Chua C-K.; Leong K-F.; Chandrasekaran M., *Trends in Biotechnology* 2004, 22, 643-652.
[3] Fang, L.; Leng, Y.; Gao, P., *Biomaterials* 2006, 27, 3701.
[4] Chang, M. C.; Ko, C-C; Douglas, W. H., *Biomaterials* 2003, 24, 2853-2862.
[5] Chen, B.; Sun, K., *Polymer Testing* 2005, 24, 978-982.
[6] Li, J.; Fartash, B.; Hermansson, L. http://www.sciencedirect.com/science?_ob=ArticleURL&_udi=B6TWB-3Y5FNW6-4X&_user=4909448&_coverDate=12%2F31%2F1995&_rdoc=1&_fmt=high&_orig=search&_origin=search&_sort=d&_docanchor=&view=c&_searchStrId=1504311677&_rerunOrigin=google&_acct=C000065612&_version=1&_urlVersion=0&_userid=4909448&md5=008743b19e3d5c7403df2-456267721d9&searchtype=a-aff3, *Biomaterials* 1995, 16, 417.
[7] Malik M. A.; Puleo D. A.; Bizios R.; Doremus R. H., *Biomaterials* 1992, 13, 123-128.
[8] Zheng, X.; Huang, M.; Ding, C. *Biomaterials* 2000, 21, 841-849.
[9] Kim, H-M; Miyaji, F; Kokubo, T; Nakamura, T., *J. of Biomed. Mat. Res.* 1996, 32, 409-417.
[10] Dervishi, E.; Li, Z.; Watanabe, F., Xu, Y.; Saini, V.; Biris, A. R.; Biris, A. S. *J. Mat. Chem.,* 2009, 19, 3004-3012.

[11] Biris A. R.; Lupu D.; Grüneis A.; Ayala P.; Rummel M. H.; Pichler T.; Li Z.; Misan I.; Dervishi E.; Biris A. S. *Chem. Mater.* 2008, 20, 3466-3472.

[12] Li, Z.; Kandel, H. R.; Dervishi, E.; Saini, V.; Biris, A. S.; Biris, A. R.; Lupu, D. *App. Phys. Lett.* 2007, 91, 5.

[13] Krishnan, A.; Dujardin, E.; Ebbesen, T. W.; Yianilos, P. N.; Treacy, M. M. J. *Phys. Rev. B* 58, 1998, 58, 14013-14019.

[14] Shokuhfar, T.; Makradi, A.; Titus, E.; Cabral, G.; Ahzi, S.; Sousa, A. C.; Belouettar, S.; Gracio, J. *J Nanosc. Nanotechnol.* 2008, 8, 4279-4284.

[15] Zhao B.; Hu H.; Mandal K.; Robert C. *Chem. Mater.* 2005, 17, 3235-3241.

[16] Liao S.; Xu G.; Wang W.; Watari F.; Cui F.; Ramakrishana S.; Chan C. K. *Acta Biomater.* 2007, 3, 669.

[17] Omori; M.; Watanabe, T.; Tanaka, M.; Okubo, A.; Kimura, H.; Hashida, T. *Nano Biomedicine* 2009, 1,137-142.

[18] White, A. A.; Kinloch, I. A.; Windle, A. H.; Best, S. M. *J. R. Soc. Interface* 2010, 7, 529-539.

[19] Lu, X.; Wang, H.; Xia, S.; Wang, J. X.; Weng, J. *Advanced Materials Research* 2009, 79, 1671.

[20] Li H.; Wang L.; Liang C.; Wang Z.; Zhao W. *Materials Science and Engineering* B 2010, 166, 19.

[21] Novoselov, K. S.; Geim, A. K.; Morozov, S. V.; Jiang, D.; Zhang, Y.; Dubonos, S. V.; Grigorieva, I. V.; Firsov, A. A., *Science* 2004, 306, 666.

[22] Fan, H.; Wang, L.; Zhao, K.; Li, N.; Shi, Z.; Ge, Z.; Jin, Z. *Biomacromolecules* 2010, 11, 2345-2351.

[23] Zhang, Y. B.; Ali, S. F.; Dervishi, E, Xu, Y.; Casciano, D.; Xu, Y.; Li, Z.; Bins. A. S. *ACS Nano* 2010, 4, 3181-3186.

[24] Lupu, D; Bins, A R; Jianu, A; Bunescu, C; Burkel, E; Indrea, E; Mihailescu, G; Pruneanu, S; Olenic, L; Misan, I. *Carbon* 2004, 42, 503-507.

[25] Bins, A. R.; Bins, A. S.; Lupu, D.; Trigwell, S.; Dervishi, E.; Rahman, Z.; Marginean, P. *Chem. Phys. Lett.* 2006, 429, 204.

[26] Sing, K. S. W.; Everett, D. H.; Haul, R. A. W.; Moscou, L.; Pierotti, R. A.; Rouquerol, J.; Siemieniewska, T. *Pure Appl. Chem.* 1985, 57, 603.

[27] Bouropoulos, N.; Stampolakis, A.; Mouzakis, D. E. *Science of Advanced Materials* 2010, 2, 239.

[28] Dervishi E.; Li Z.; Shyaka J.; Watanabe F.; Biswas A.; Umwungeri J. L.; Courte A.; Bins A. R.; Kebdani O.; Bins A. S. *Chem. Phys. Lett.* 2011, 301, 390.

[29] Moon, J.-M.; An, K. H.; Lee, Y. H.; Park, Y. S.; Bae, D. J. *J. Phys. Chem. B* 2001, 105, 5677.

[30] Dillon, A. C.; Gennett, T.; Jones, K. M.; Alleman, J. L.; Parilla, P. A.; Heben, M. J. *Adv. Mater.* 1999, 11, 1354.

[31] Gregg S. B.; Vecchio S. *J. Phys. Chem. B* 2006, 110, 1179-1186

[32] Ramesh P.; Okasaki T.; Sugai T.; Kimura J.; Kishi N.; Sato K; Ozeki Y.; Shinohara H. *Chem. Phys. Lett.* 2006, 418, 408.

[33] Dresselhaus M. S.; Jorio A.; Hofmann M.; Dresselhaus G.; Saito R. *Nano Letters,* 2010, 10, 751-758.

[34] Hojati-Talemi P.; Simon G. P. *Carbon* 2010, 48, 3993.

[35] Park J. S.; Reina A.; Saito R.; Kong J.; Dresselhaus G.; Dresselhaus M. S. *Carbon* 2009, 47, 1303.

[36] Ferrari A. C. *Solid State Communications* 2007, 143, 47.

[37] De Aza, P. N.; Guitián, F.; Santos, C.; De Aza, S.; Cuscó, R.; Artús, L. *Chem. Mater.* 1997, 9, 916.

[38] Zanello L. P.; Zhao B.; Hu H., Haddon R. C. *Nano Letters* 2006, 6, 562.

[39] Mahmood M.; Fejleh P.; Karmakar A.; Fejleh A.; Xu Y.; Kannarpady G.; Ishihara H.; Sharma R.; Li Z.; Ghosh A.; et al. *Adv. Engin. Mat.* 2011, 13, B95-B101 DOI: 10.1002/adem.201080072.

What is claimed is:

1. A multicomponent and biocompatible nanocomposite material, comprising:
   (a) a graphene structure formed with a plurality of graphene layers; and
   (b) gold/hydroxyapatite (Au/HA) nanoparticles distributed within the graphene structure, wherein the Au/HA nanoparticles comprise HA structures and Au nanoparticles deposited over surfaces of the HA structures,
   wherein the nanocomposite material is formed by heating an Au/HA catalyst thin film in a reactor with a carbon source gas to perform radio frequency chemical vapor deposition (RF-CVD), wherein the nanocomposite material has a flattened structure with rounded edges, and comprises a graphene matrix and is applied in an area of bone regeneration, and wherein the Au/HA nanoparticles are formed by Au/HA catalyst and distributed within the graphene matrix.

2. The nanocomposite material of claim 1, wherein the carbon source gas comprises acetylene ($C_2H_2$).

3. The nanocomposite material of claim 1, wherein the carbon source gas comprises methane ($CH_4$).

4. The nanocomposite material of claim 1, wherein the Au/HA catalyst thin film is formed by:
   (a) immersing HA nanocrystals and gold trichloride trihydrate ($HAuCl_4 \cdot 3H_2O$) in water to form a mixture;
   (b) stirring the mixture at a stirring temperature such that the Au nanoparticles deposits on the HA nanocrystals;
   (c) drying the mixture at a drying temperature to obtain the Au/HA catalyst; and
   (d) distributing the Au/HA catalyst to form the Au/HA catalyst thin film.

5. The nanocomposite material of claim 4, wherein the stirring temperature is about 70-90° C., and the drying temperature is about 100° C.

6. The nanocomposite material of claim 1, wherein the first flow rate is about 150-600 ml/min, and the first period is about 5-20 minutes, and the first temperature is about 400-600° C.

7. The nanocomposite material of claim 6, wherein the third flow rate is about 5-30 ml/min, and the third time is about 15-90 minutes.

8. The nanocomposite material of claim 6, wherein the third flow rate is about 40-240 ml/min, and the third time is about 15-60 minutes.

9. The nanocomposite material of claim 1, wherein Au nanoclusters are uniformly arranged over the surfaces of HA particles with diameters between about 2 nm and 7 nm.

10. The nanocomposite material of claim 1, wherein the Au nanoparticles have uniform sizes and slightly elliptic shapes with average minor and major dimensions of about 3.6±0.5 nm and about 4.1±0.5 nm, respectively.

11. The nanocomposite material of claim 1, wherein the heating the Au/HA catalyst thin film in the reactor comprising:
   introducing an inert gas to the reactor at a first flow rate for a first time;
   heating the reactor to a first temperature;
   introducing hydrogen to the reactor at a flow rate about 50-300 ml/min for 5-20 minutes;
   heating the reactor to a second temperature from 750° C. to 810° C. or from 900° C. to 1000° C. or;

introducing the carbon source gas to the reactor at a third flow rate for a third time; and cooling the reactor.

\* \* \* \* \*